United States Patent
Yoo et al.

(10) Patent No.: US 11,469,378 B2
(45) Date of Patent: Oct. 11, 2022

(54) ELECTROLUMINESCENT COMPOUND AND ELECTROLUMINESCENT DEVICE INCLUDING THE SAME

(71) Applicants: LG Display Co., Ltd., Seoul (KR); PnH Tech, Yongin-si (KR)

(72) Inventors: Seon-Keun Yoo, Paju-si (KR); Hee-Jun Park, Paju-si (KR); Jeong-Dae Seo, Paju-si (KR); Seo-Yong Hyun, Yongin-si (KR); Ha-Yeon Kim, Suwon-si (KR); Seok-Keun Yoon, Hwaseong-si (KR); Sun-Gi Kim, Yongin-si (KR); In-Ho Lee, Suwon-si (KR)

(73) Assignees: LG DISPLAY CO., LTD., Seoul (KR); PNH TECH, Yongin-si (KR)

( * ) Notice: Subject to any disclaimer, the term of this patent is extended or adjusted under 35 U.S.C. 154(b) by 462 days.

(21) Appl. No.: 16/436,603

(22) Filed: Jun. 10, 2019

(65) Prior Publication Data
US 2019/0378981 A1    Dec. 12, 2019

(30) Foreign Application Priority Data
Jun. 11, 2018 (KR) .................. 10-2018-0066766

(51) Int. Cl.
| | |
|---|---|
| *H01L 51/00* | (2006.01) |
| *C09K 11/06* | (2006.01) |
| *C07D 307/91* | (2006.01) |
| *C07C 211/61* | (2006.01) |
| *C07D 213/22* | (2006.01) |
| *C07C 211/54* | (2006.01) |
| *H01L 51/50* | (2006.01) |

(52) U.S. Cl.
CPC .......... *H01L 51/006* (2013.01); *C07C 211/54* (2013.01); *C07C 211/61* (2013.01); *C07D 213/22* (2013.01); *C07D 307/91* (2013.01); *C09K 11/06* (2013.01); *H01L 51/0058* (2013.01); *H01L 51/0061* (2013.01); *H01L 51/0067* (2013.01); *C07C 2603/18* (2017.05); *C09K 2211/1007* (2013.01); *C09K 2211/1011* (2013.01); *C09K 2211/1014* (2013.01); *C09K 2211/1018* (2013.01); *H01L 51/0052* (2013.01); *H01L 51/0073* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01)

(58) Field of Classification Search
None
See application file for complete search history.

(56) References Cited

U.S. PATENT DOCUMENTS

| | | | | |
|---|---|---|---|---|
| 2009/0167162 | A1* | 7/2009 | Lin | ...................... H01L 51/0085 313/504 |
| 2011/0084291 | A1* | 4/2011 | Jeong | ..................... H01L 51/524 257/89 |
| 2014/0197381 | A1 | 7/2014 | Kim et al. | |
| 2015/0041780 | A1* | 2/2015 | Ma | ........................ H01L 51/504 257/40 |
| 2015/0155491 | A1† | 6/2015 | Mujica-Fernaud | |
| 2015/0228932 | A1* | 8/2015 | Ma | ...................... H01L 51/5016 257/40 |
| 2015/0295181 | A1† | 10/2015 | Mujica-Fernaud | |
| 2016/0043325 | A1† | 2/2016 | Gorohmaru | |
| 2016/0072078 | A1* | 3/2016 | Lee | ..................... H01L 51/0071 257/40 |
| 2016/0133880 | A1* | 5/2016 | Lee | ..................... H01L 51/5281 257/40 |

(Continued)

FOREIGN PATENT DOCUMENTS

| | | |
|---|---|---|
| EP | 1 013 740 A2 | 6/2000 |
| JP | 2004-231547 A | 8/2004 |

(Continued)

OTHER PUBLICATIONS

Wang et al. "Practical access to 1,3,5-triarylbenzenes from chalcones and DMSO" RSC Adv. 2015, 5, 73180-73183. (Year: 2015).*
CAS 1136694-40-2, STN Registry, Dec. 3, 2009.
CAS 1233141-16-6, STN Registry, Jul. 20, 2010.
CAS 1245339-64-3, STN Registry, Oct. 11, 2010.

(Continued)

*Primary Examiner* — Robert S Loewe
(74) *Attorney, Agent, or Firm* — Birch, Stewart, Kolasch & Birch, LLP

(57) ABSTRACT

The present invention provides an electroluminescent compound of one of following formulas Formula 1 and Formula 2. Another aspect of the invention is an electroluminescent device including a first electrode; a second electrode facing the first electrode; and at least one organic material layer between the first and second electrodes, wherein one or more of the at least one organic material layer includes the electroluminescent compound.

[Formula 1]

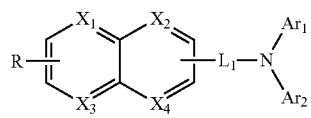

[Formula 2]

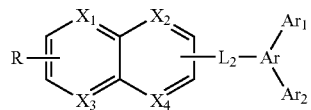

13 Claims, No Drawings

(56) References Cited

U.S. PATENT DOCUMENTS

| | | | |
|---|---|---|---|
| 2016/0149141 A1* | 5/2016 | Jung | H01L 51/0073 257/40 |
| 2017/0012204 A1* | 1/2017 | Jin | H01L 51/0072 |
| 2017/0040535 A1* | 2/2017 | Ogita | C09K 11/06 |
| 2017/0062734 A1* | 3/2017 | Suzuki | H01L 51/0072 |
| 2017/0092870 A1* | 3/2017 | Kim | H01L 51/0052 |
| 2017/0170403 A1* | 6/2017 | Cho | C09K 11/025 |
| 2017/0179204 A1* | 6/2017 | Lim | H01L 51/0052 |
| 2017/0288147 A1 | 10/2017 | Fujita et al. | |
| 2018/0033993 A1* | 2/2018 | Seo | H01L 51/006 |
| 2018/0114907 A1† | 4/2018 | Takada | |
| 2018/0287069 A1* | 10/2018 | Cha | H01L 51/006 |
| 2019/0051856 A1* | 2/2019 | Kim | H01L 51/0073 |
| 2019/0189927 A1* | 6/2019 | Lee | H01L 51/0071 |
| 2019/0241548 A1* | 8/2019 | Park | C07D 405/04 |
| 2020/0212310 A1* | 7/2020 | Kim | C09K 11/06 |
| 2021/0175435 A1* | 6/2021 | Kadoma | C07D 209/80 |

FOREIGN PATENT DOCUMENTS

| | | | | |
|---|---|---|---|---|
| JP | WO2007/125714 A1 | | 11/2007 | |
| JP | WO2009/145016 A1 | | 12/2009 | |
| JP | 4411708 B2 | | 2/2010 | |
| JP | 2012-97091 A | | 5/2012 | |
| JP | 5420310 B2 | | 2/2014 | |
| KR | 1020110049554 | * | 5/2011 | C09K 11/06 |
| KR | 10-2015-0023657 A | | 3/2015 | |
| KR | 10-1530049 B1 | | 6/2015 | |
| KR | 10-2016-0149975 A | † | 12/2016 | |
| KR | 1020170058618 | * | 5/2017 | C07D 403/04 |
| KR | 10-2018-0044799 A | | 5/2018 | |
| WO | WO-2010126270 A1 | * | 11/2010 | C07D 413/10 |
| WO | WO 2016/190600 A1 | | 12/2016 | |
| WO | 2017146466 A1 | † | 8/2017 | |
| WO | WO-2018016742 A1 | * | 1/2018 | C07D 307/91 |
| WO | WO 2016/032137 A1 | | 3/2018 | |

OTHER PUBLICATIONS

CAS 1253970-37-4, STN Registry, Nov. 20, 2010.
CAS 1481692-54-9, STN Registry, Nov. 26, 2013.
CAS 1481695-22-0, STN Registry, Nov. 26, 2013.
CAS 2036263-25-5, STN Registry, Nov. 23, 2016.
CAS 2055763-57-8, STN Registry, Jan. 10, 2017.
CAS 2061992-86-5, STN Registry, Jan. 30, 2017.
CAS 2061393-03-9, STN Registry, Jan. 30, 2017.
CAS 2061993-04-0, STN Registry, Jan. 30, 2017.
CAS 2061993-15-3, STN Registry, Jan. 30, 2017.
CAS 2079057-28-4, STN Registry, Mar. 1, 2017.
CAS 2165371-81-1, STN Registry, Dec. 27, 2017.
CAS 2169955-67-1, STN Registry, Jan. 7, 2018.
CAS 2179125-17-6, STN Registry, Feb. 22, 2018.
CAS 656222-28-5, STN Registry, Mar. 1, 2004.
CAS 792924-35-7, STN Registry, Dec. 6, 2004.

\* cited by examiner
† cited by third party

ELECTROLUMINESCENT COMPOUND AND ELECTROLUMINESCENT DEVICE INCLUDING THE SAME

CROSS-REFERENCE TO RELATED APPLICATIONS

The present application claims the benefit of Korean Patent Application No. 10-2018-0066766 filed in the Republic of Korea on Jun. 11, 2018, which is hereby incorporated by reference in its entirety.

BACKGROUND

Field of Technology

The present disclosure relates to an electroluminescent compound, and more particularly, to an electroluminescent compound having an improved lifespan and emitting efficiency and an electroluminescent device including the same.

Discussion of the Related Art

The electroluminescent (EL) device is formed on a transparent substrate and can be operated at a voltage (e.g., 10V or below) lower than a voltage required to operate other display devices, e.g., plasma display panels. In addition, the EL device has lower power consumption and excellent color purity. Moreover, since the EL device can emit red light, green light and blue light, the EL device is developed as next generation display device.

To provide the above advantages, a material including, e.g., a hole injection material, a hole transporting material, an emitting material, an electron transporting material or an electron injection material, having high reliability and efficiency is needed. However, the materials in the prior art are insufficient, and a new material is required.

Recently, not only is there a need for enhancing the properties of an EL device by changing the material in an organic layer but also a need for enhancing the color purity and the emitting efficiency by optimizing an optical thickness between the anode an the cathode. For example, a capping layer may be used on an electrode to enhance the color purity and the emitting efficiency of the EL device.

The development of the device structure and new material for enhancing the emitting property of the EL device is required.

SUMMARY

The present invention is directed to an EL compound and an EL device including the same that substantially obviate one or more of the problems associated with the limitations and disadvantages of the related conventional art.

Additional features and advantages of the disclosure are set forth in the description which follows, and will be apparent from the description, or evident by practice of the invention. The objectives and other advantages of the invention are realized and attained by the features described herein as well as in the appended drawings.

To achieve these and other advantages in accordance with the purpose of the embodiments of the invention, as described herein, an aspect of the invention is an electroluminescent compound of Formula 1 or Formula 2:

[Formula 1]

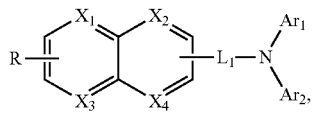

[Formula 2]

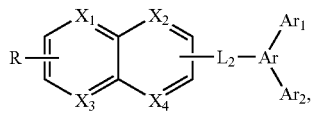

wherein each of $X_1$ to $X_4$ is independently N or CR', wherein each of R and R' is independently selected from the group consisting of hydrogen, deuterium, cyano group, hydroxyl group, halogen, substituted or non-substituted C1 to C10 alkyl group, substituted or non-substituted C6 to C20 aryl group and substituted or non-substituted C3 to C30 heteroaryl group, wherein each of $L_1$ and $L_2$ is independently selected from a single bond, substituted or non-substituted C6 to C20 arylene group and substituted or non-substituted C3 to C30 heteroarylene group, and wherein each of Ar1 and Ar2 is independently selected from the group consisting of substituted or non-substituted C6 to C20 aryl group and substituted or non-substituted C3 to C30 heteroaryl group.

Another aspect of the invention is an electroluminescent device including a first electrode; a second electrode facing the first electrode; and at least one organic material layer between the first and second electrodes, wherein one or more of the at least one organic material layer includes the electroluminescent compound.

It is to be understood that both the foregoing general description and the following detailed description are exemplary and explanatory and are intended to further explain the invention as claimed.

DETAILED DESCRIPTION

Reference will now be made in detail to some of the examples and preferred embodiments.

An electroluminescent (EL) compound of the present disclosure is represented by Formula 1 or Formula 2. The EL compound is included in a hole transporting layer (HTL) of an EL device such that the properties, e.g., the emitting efficiency, the driving property or the lifespan, of the EL device are improved. In addition, the EL compound may be included in a light-efficiency enhancing layer, which is formed on a side of a lower electrode or an upper electrode to be opposite to an organic layer of the EL device, such that the light efficiency of the EL device is significantly improved. As a result, the EL device including the EL compound has advantages in the emitting efficiency, the driving voltage, the color purity and the lifespan.

[Formula 1]

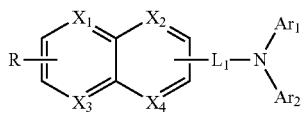

[Formula 2]

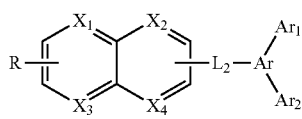

In Formula 1 and Formula 2, each of $X_1$ to $X_4$ is independently N or CR'. Each of R and R' is independently selected from the group consisting of hydrogen, deuterium, cyano group, hydroxyl group, halogen, substituted or non-substituted C1 to C10 alkyl group, substituted or non-substituted C6 to C20 aryl group and substituted or non-substituted C3 to C30 heteroaryl group.

Each of $L_1$ and $L_2$ is independently selected from a single bond, substituted or non-substituted C6 to C20 arylene group and substituted or non-substituted C3 to C30 heteroarylene group. For example, each of $L_1$ and $L_2$ may be selected from Formula 3a and Formula 3b.

Each of $Ar_1$ and $Ar_2$ is independently selected from the group consisting of substituted or non-substituted C6 to C20 aryl group and substituted or non-substituted C3 to C30 heteroaryl group.

Ar is selected from the group consisting of substituted or non-substituted C6 to C20 arylene group and substituted or non-substituted C3 to C30 heteroarylene group. For example, Ar may be Formula 4.

[Formula 3a]

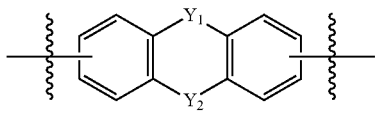

[Formula 3b]

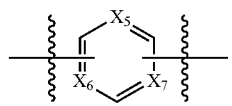

[Formula 4]

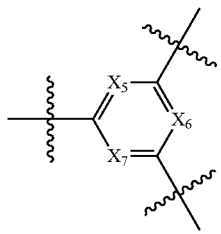

In Formula 3a, Formula 3b and Formula 4, each of $X_5$ to $X_7$ is independently N or $CR_1$. Each of $Y_1$ and $Y_2$ is independently selected from a single bond, O, S, Se, —$R_4$—Si—$R_2$—, $R_5$—C—$R_3$—. Each of $R_1$, $R_2$, $R_3$, $R_4$ and $R_5$ is independently selected from the group consisting of hydrogen, deuterium, cyano group, hydroxyl group, halogen, substituted or non-substituted C1 to C10 alkyl group, substituted or non-substituted C6 to C20 aryl group and substituted or non-substituted C3 to C30 heteroaryl group.

The term of "substituted" in "substituted or non-substituted" may mean that each of $L_1$, $L_2$, Ar, $Ar_1$, $Ar_2$ and so on may be further substituted by at least one substituent. In this instance, the substituent may be selected from the group consisting of deuterium, cyano group, halogen, amino group, hydroxyl group, nitro group, C1 to C10 alkyl group, C1 to C10 halogenated alkyl group, C6 to C20 aryl group, C3 to C30 heteroaryl group, C1 to C10 alkoxy group, C1 to C10 alkylsilyl group and C6 to C20 arylsilyl group.

In the present disclosure, the examples of the substituent may be follows, but it is not limited thereto.

In the present disclosure, alkyl group may have linear or branched structure. For example, alkyl group may be selected from the group consisting of methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, iso-pentyl, neopentyl, tert-pentyl, hexyl, n-hexyl, 1-methyl-pentyl and 2-methyl-pentyl, but it is not limited thereto.

Aryl group may have mono-cyclic or poly-cyclic structure. For example, aryl group may be selected from the group consisting of phenyl, biphenl, terphenyl, stilbene, naphthyl, anthracenyl, phenanthrenyl, pyrenyl, perylenyl, tetracenyl, chrysenyl, fluorenyl, triphenylenyl and fluoranthenyl, but it is not limited thereto.

Heteroaryl group may include a hetero-atom, e.g., 0, N or S. For example, heteroaryl group may be selected from the group consisting of thiophenyl, furanyl, pyrrolyl, imidazolyl, thiazolyl, oxazolyl, oxadiazolyl, triazolyl, pyridyl, bipyridyl, pyrimidyl, triazinyl, acrydinyl, pyridazinyl, pyrazinyl, quinolinyl, quinazolinyl, quinoxazinyl, phthalazinyl, pyridopyrimidinyl, pyridopyrazinyl, pyrazino pyrazinyl, isoquinolinyl, indolyl, carbazolyl, benzo-oxazolyl, benzo-imidazolyl, benzo-thiazolyl, benzo-carbazolyl, benzothiophenyl, dibenzothiophenyl, benzofuranyl, dibenzofuranyl, phenanthrolinyl, thiazolyl, iso-oxathiazolyl, oxadiazolyl, thiadiazolyl and phenothiazyl, but it is not limited thereto.

Aryl in arylsilyl group may be same as the above aryl group, and halogen may be fluorine, chlorine, bromine or iodine.

Silyl group may be selected from the group consisting of trimethylsilyl, triethylsilyl, t-butyl-dimethylsilyl, vinyl-dimethylsilyl, propyl-dimethylsilyl, triphenylsilyl, diphenylsilyl and phenylsilyl, but it is not limited thereto.

Halogen as the substituent may be fluorine, chlorine or bromine.

The EL compound of the present disclosure of Formula 1 or Formula 2 may be used to an organic layer of the EL device due to the structural distinguishment. For example, the EL compound as an organic compound may be used as a hole transporting material or a material of a light-efficiency enhancing layer formed at a side of the electrodes of the EL device.

For example, the EL compound of Formula 1 or Formula 2 may be one of compounds of Formula 5, but it is not limited thereto.

[Formula 5]

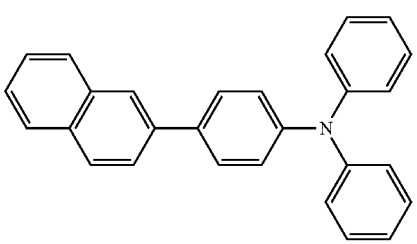

1

-continued
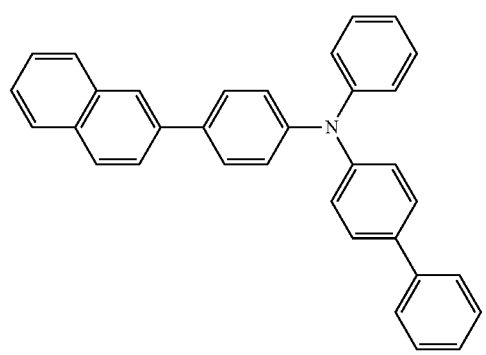
2
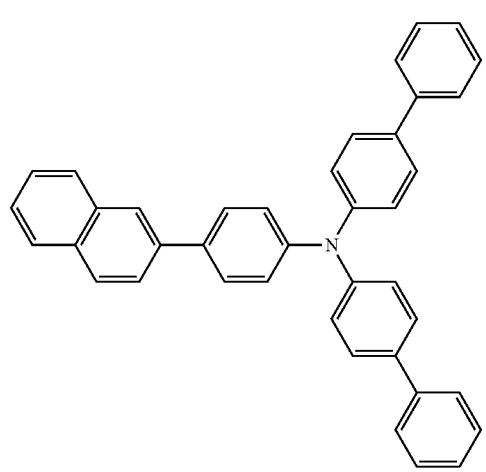
3
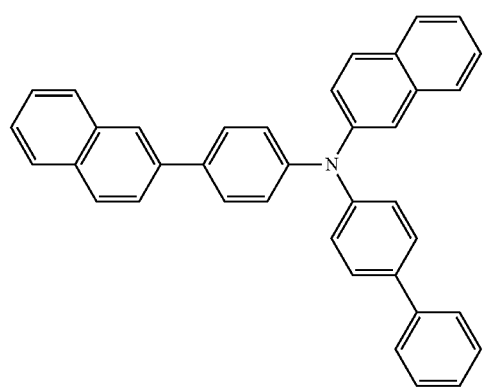
4
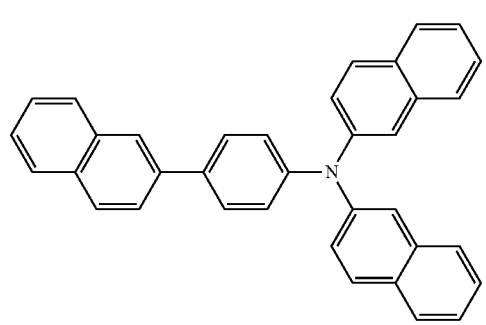
5
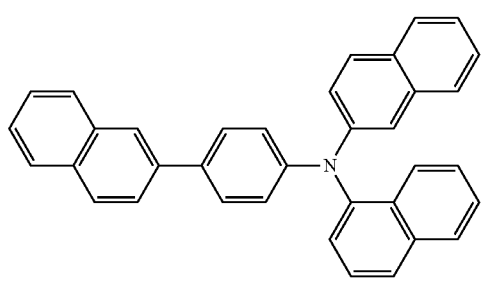
6
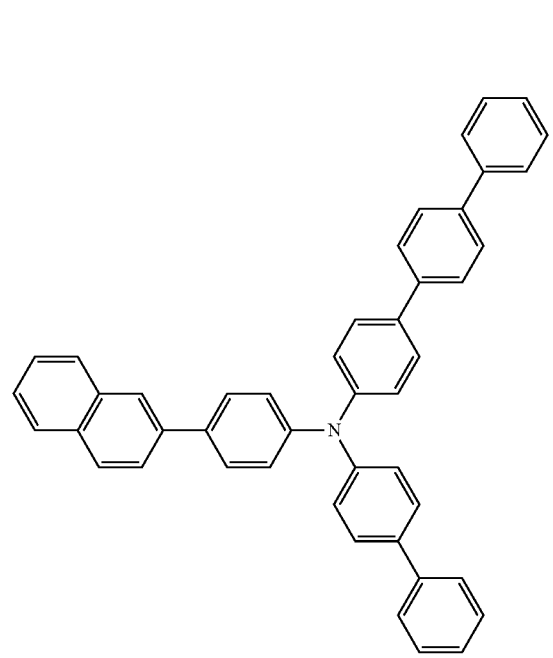
7
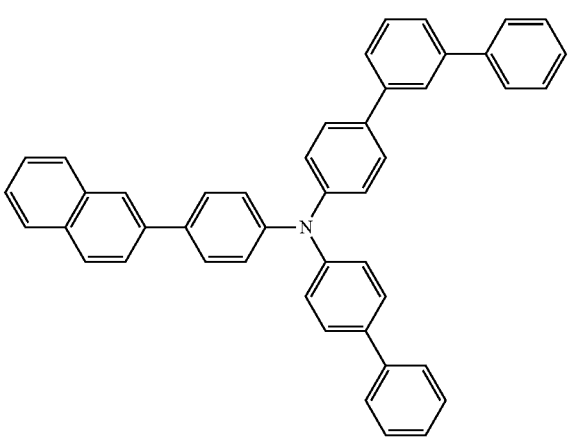
8

9
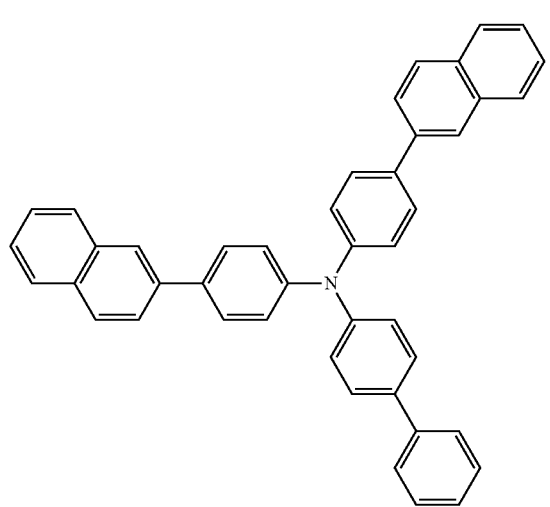
10
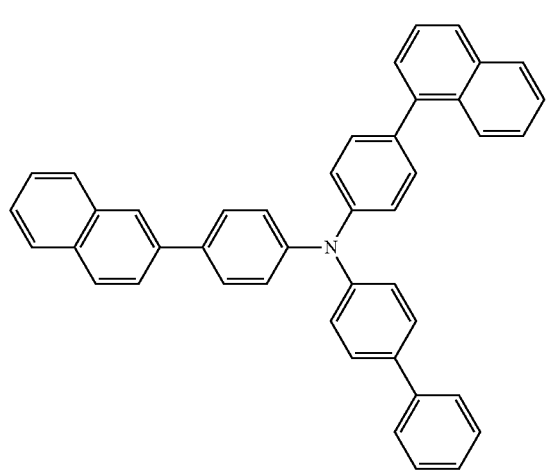
11
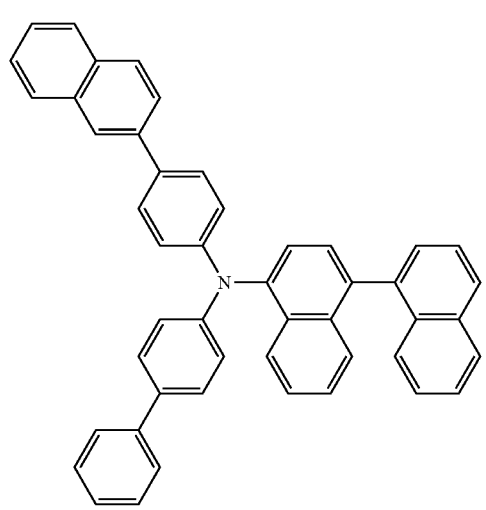
12
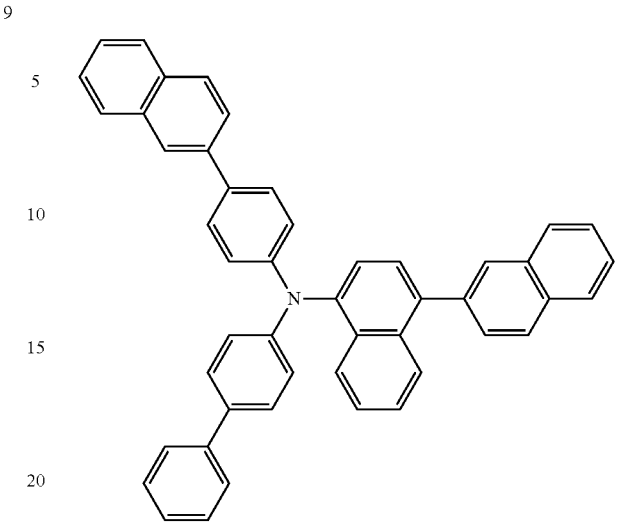
13
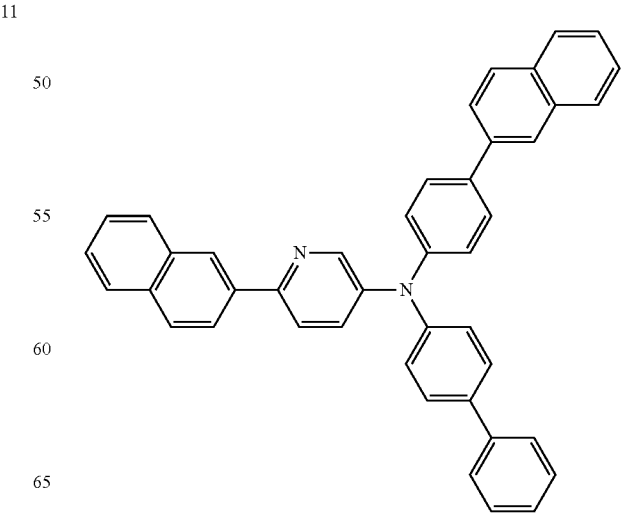
14

15
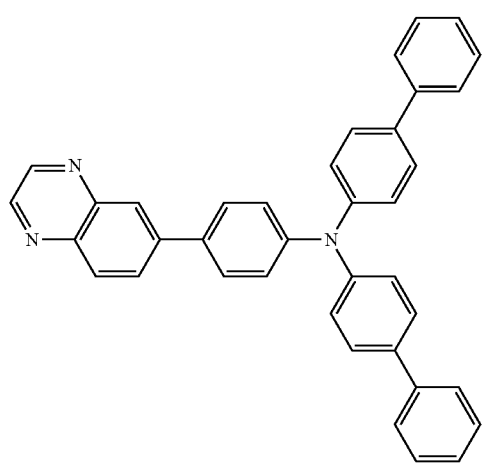
16
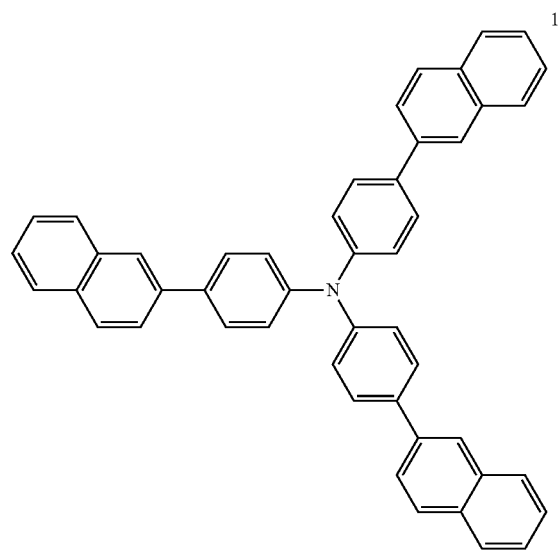
17
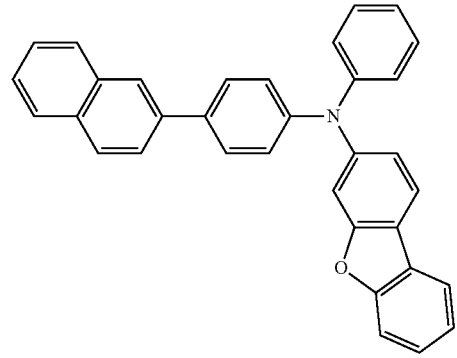
18
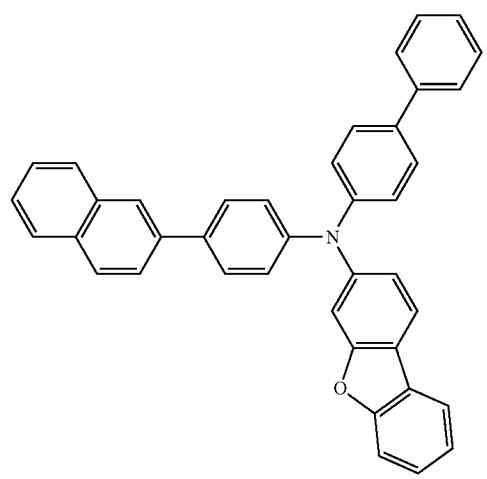
19
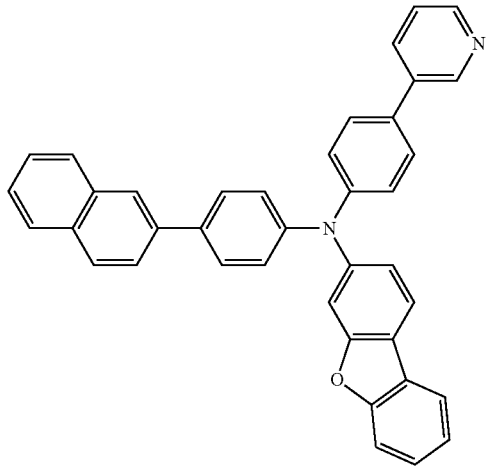
20
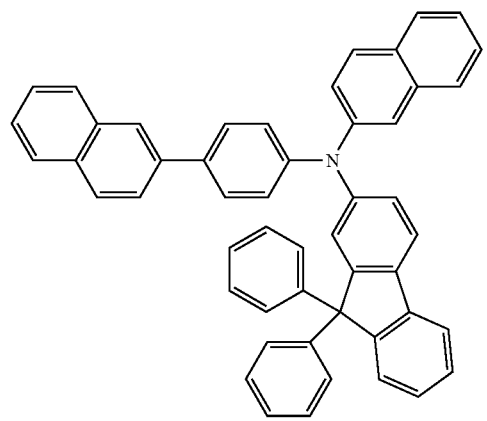

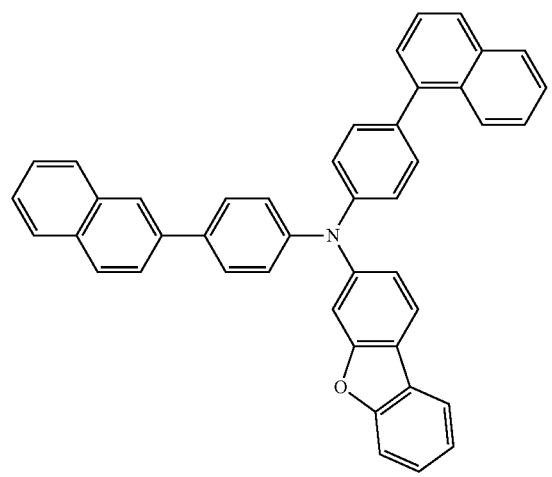
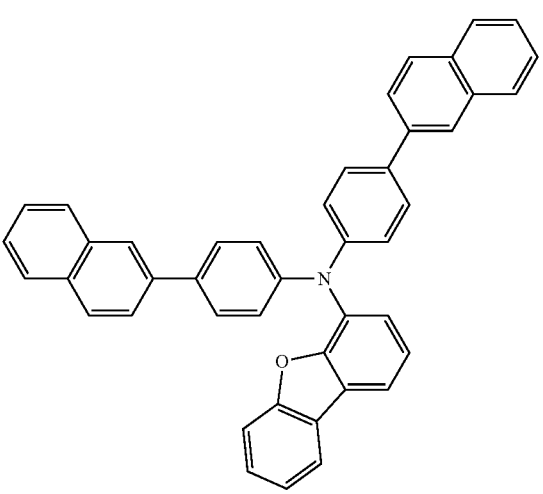

26
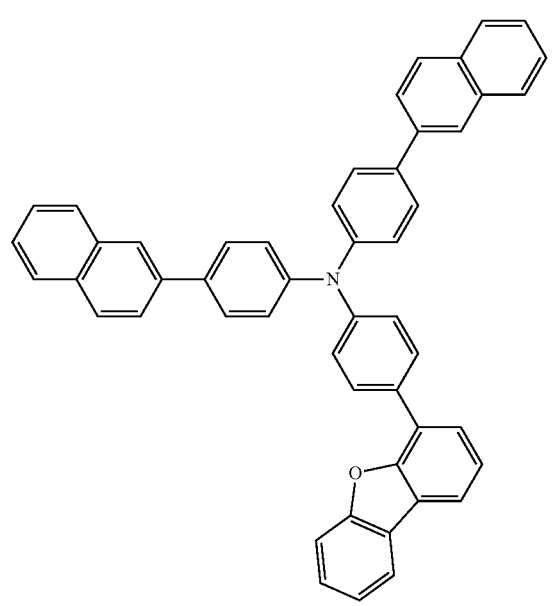
27
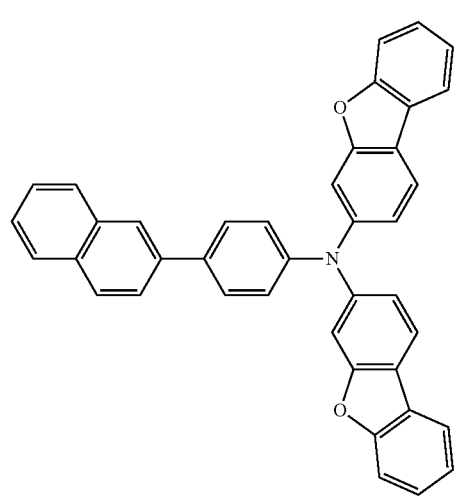
28
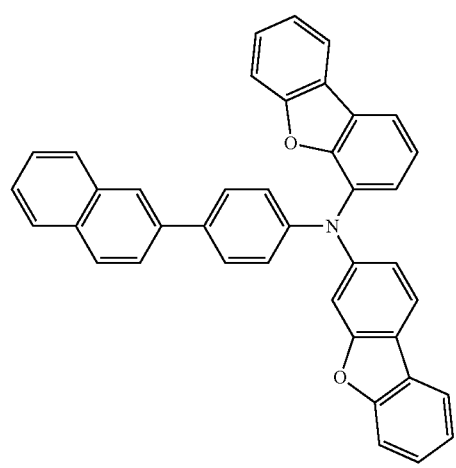
29
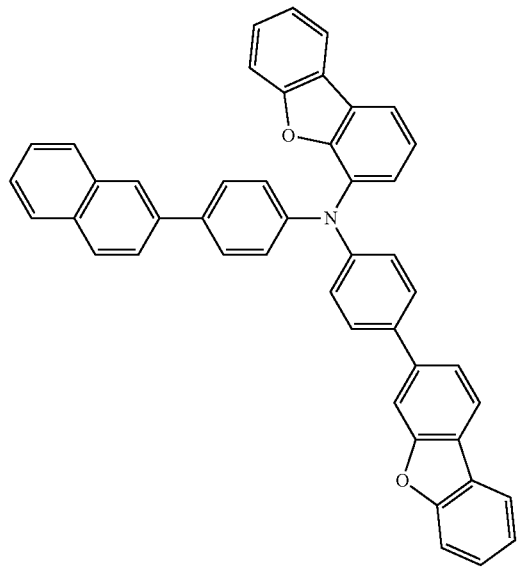
30
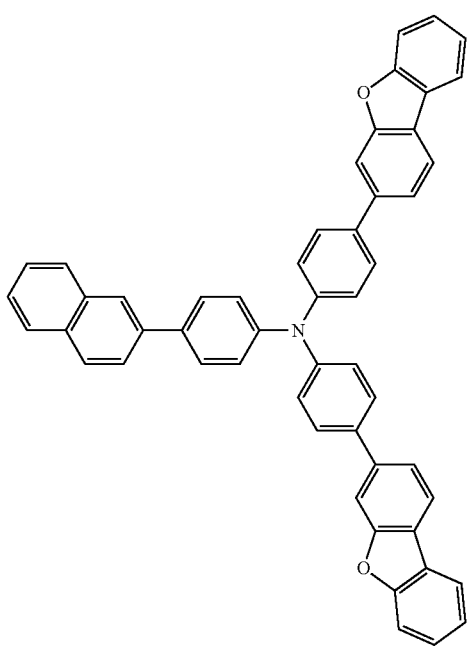
31
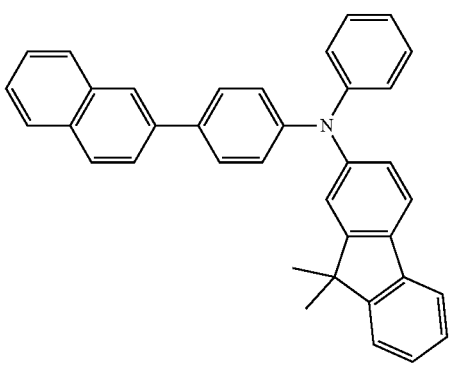

32
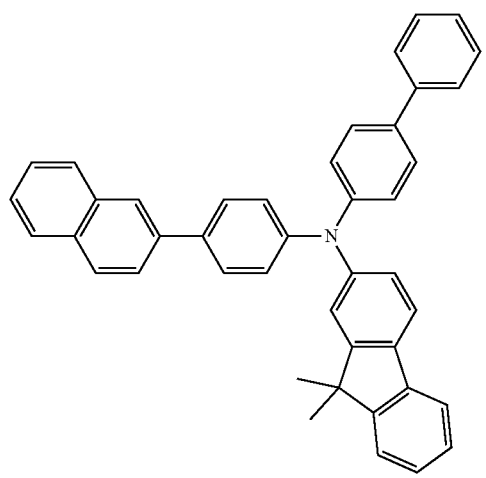
35
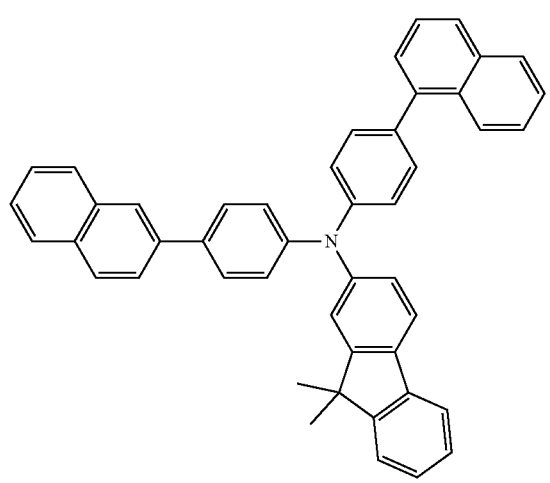
33
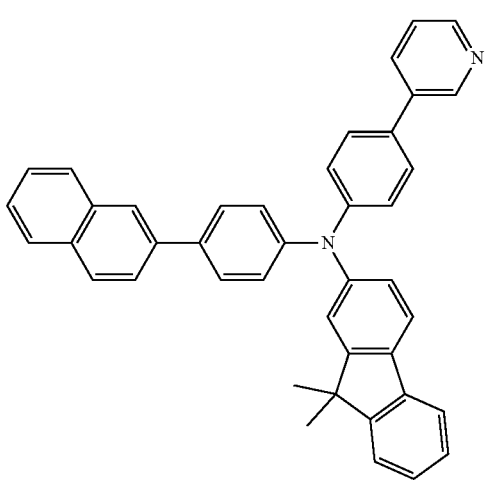
36
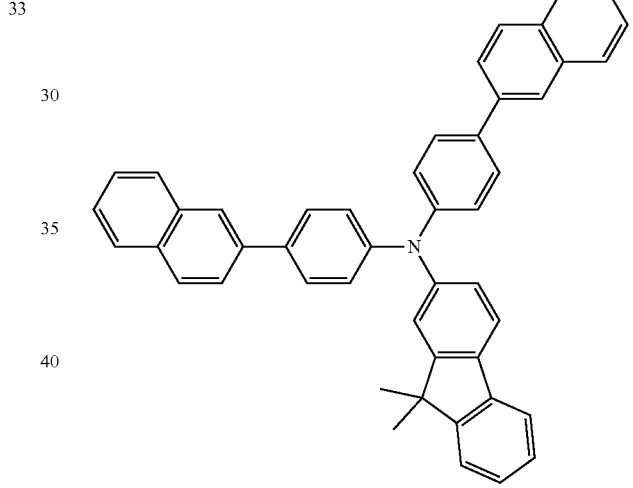
34
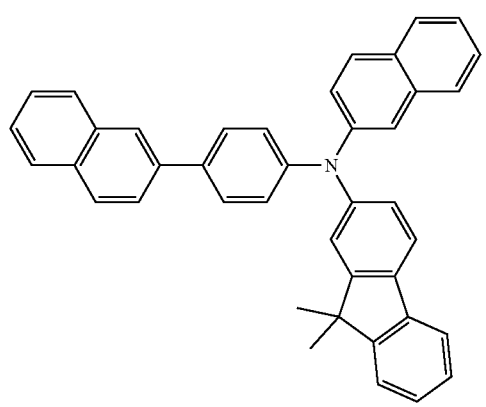
37
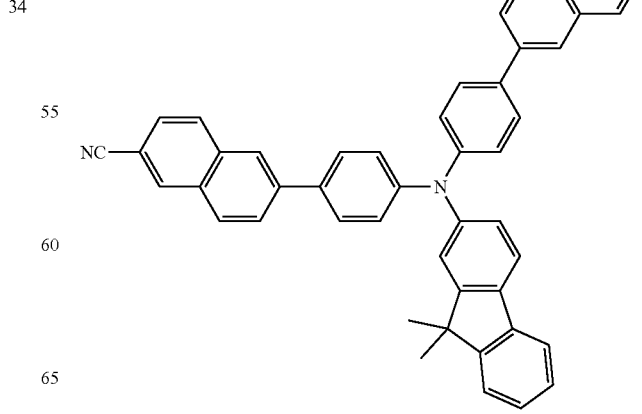

38
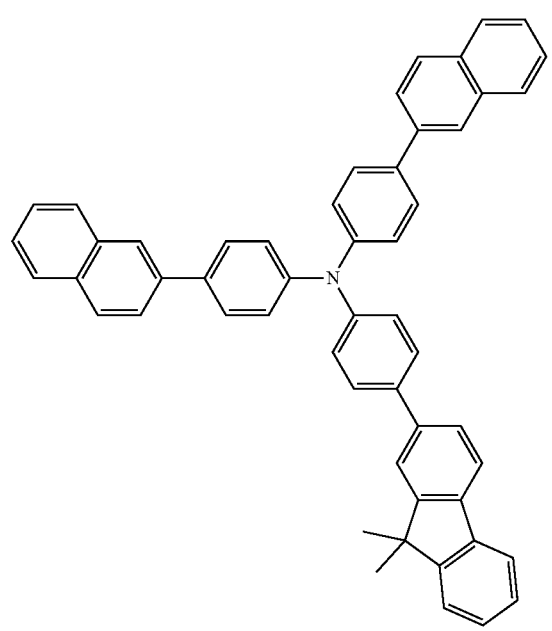
39
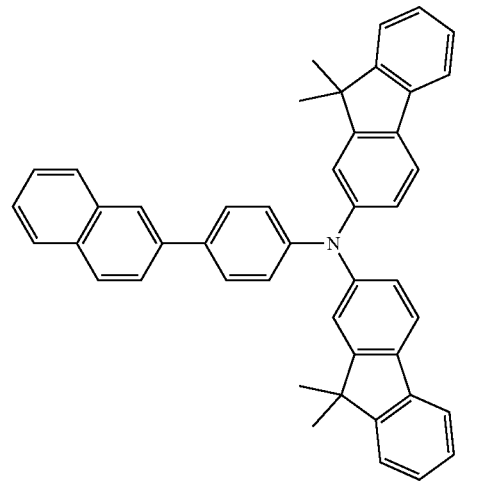
40
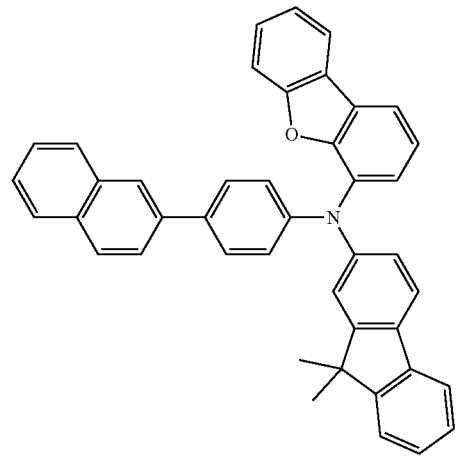
41
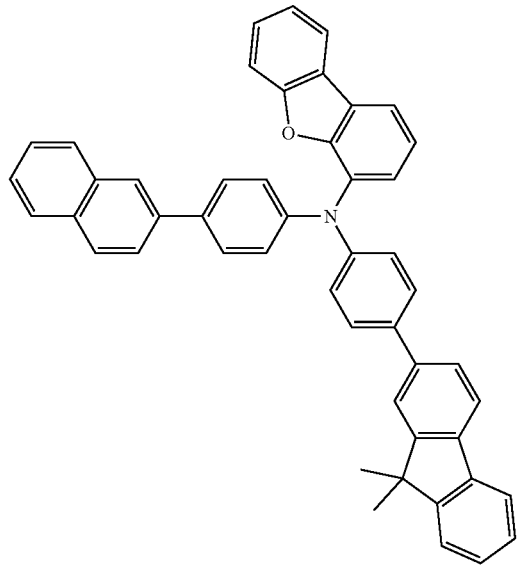
42
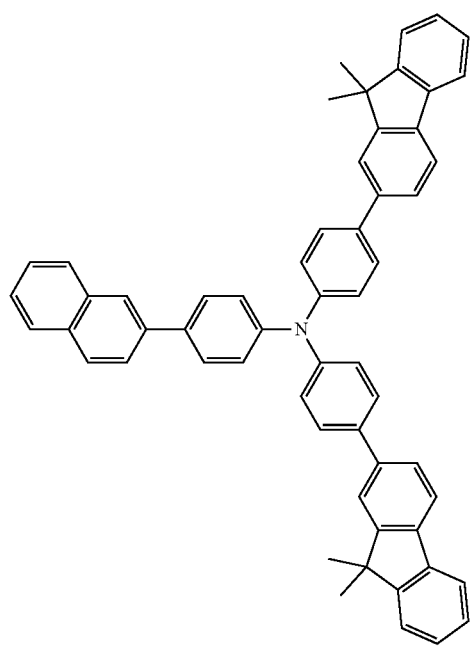

43
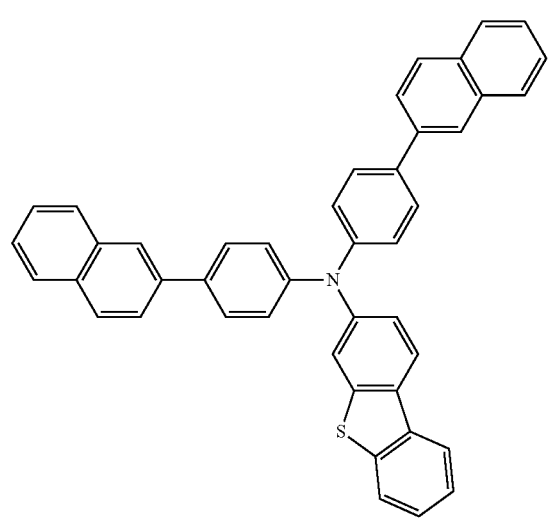
44
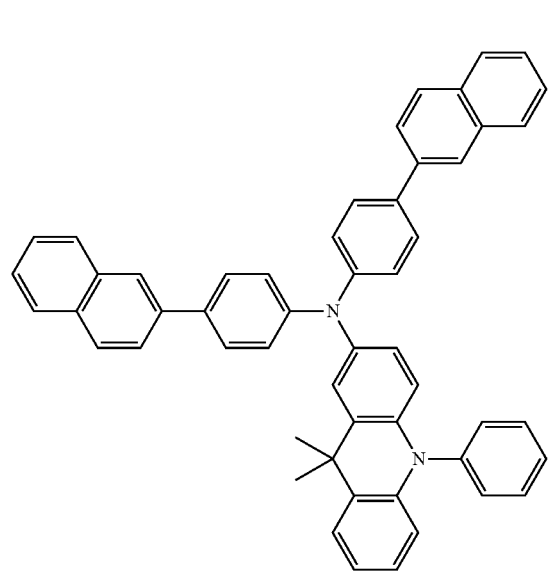
45
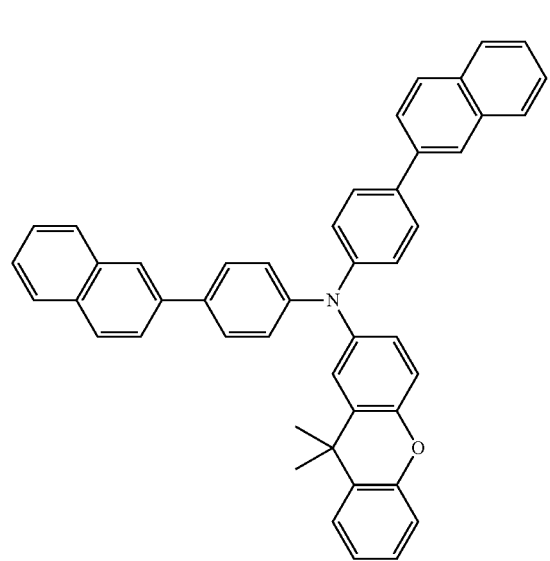
46
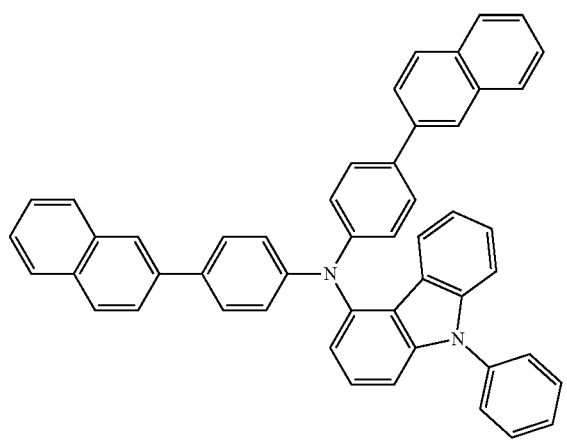
47
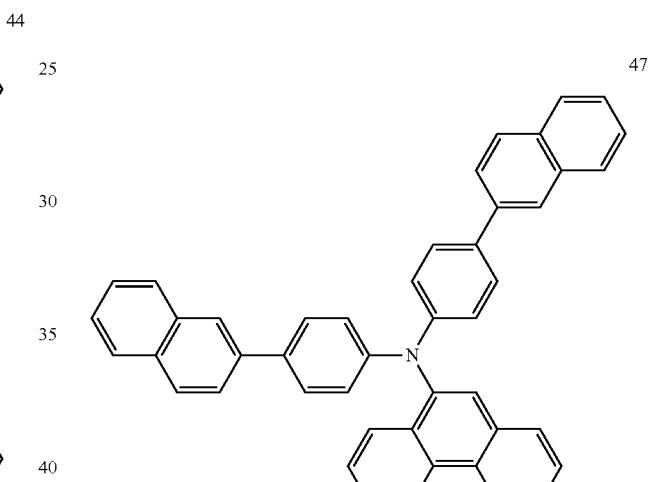
48
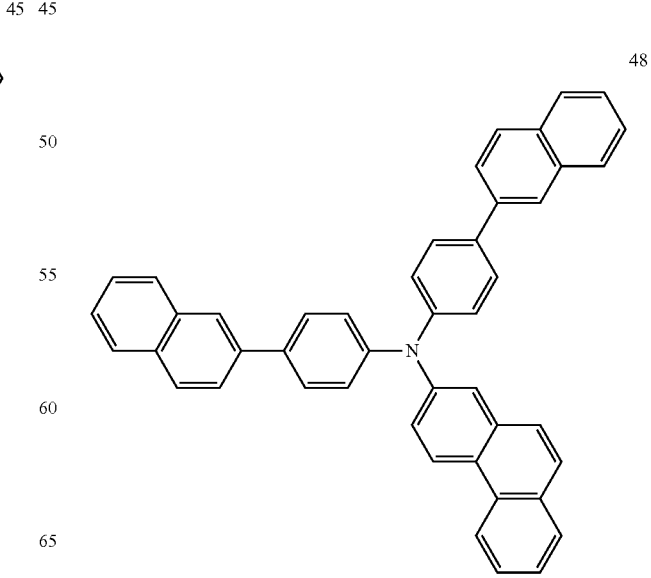

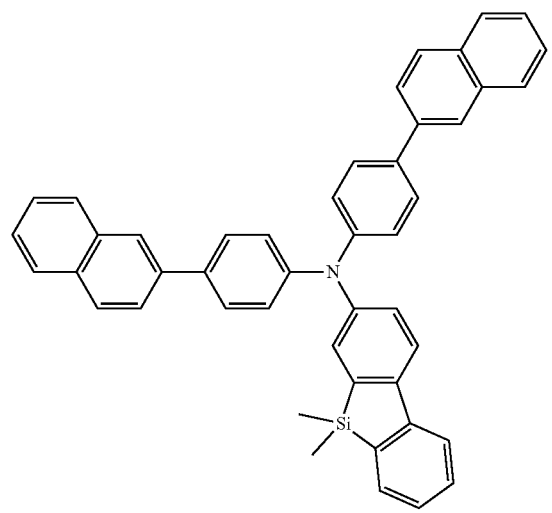
49
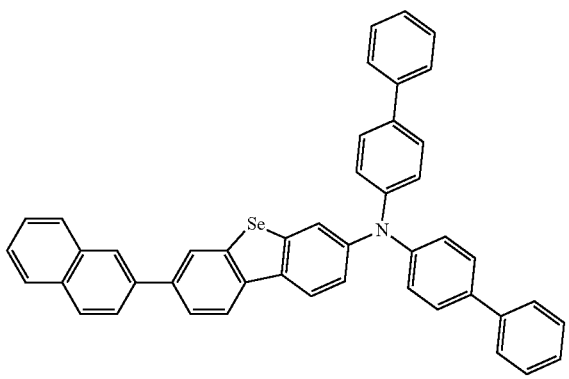
52
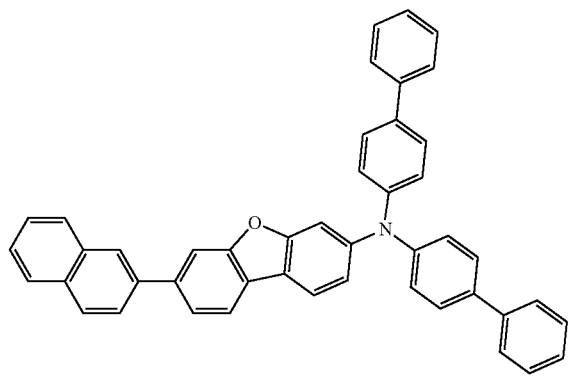
50
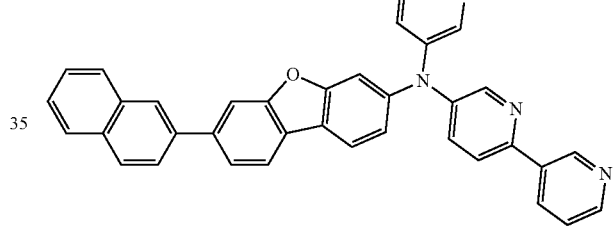
53
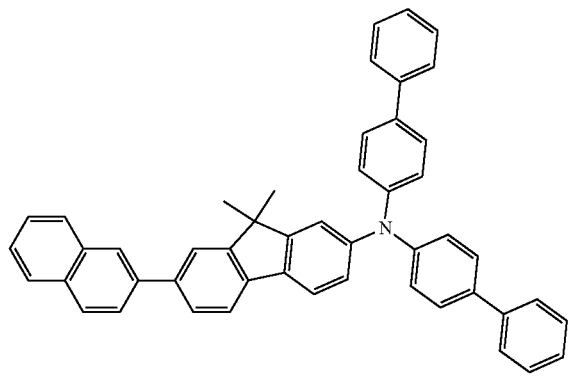
51
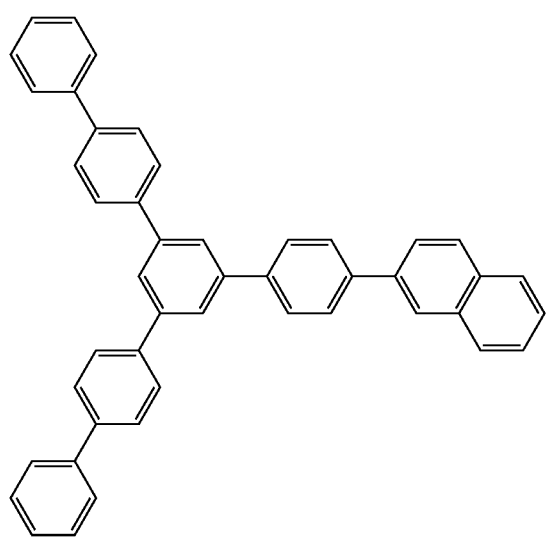
54

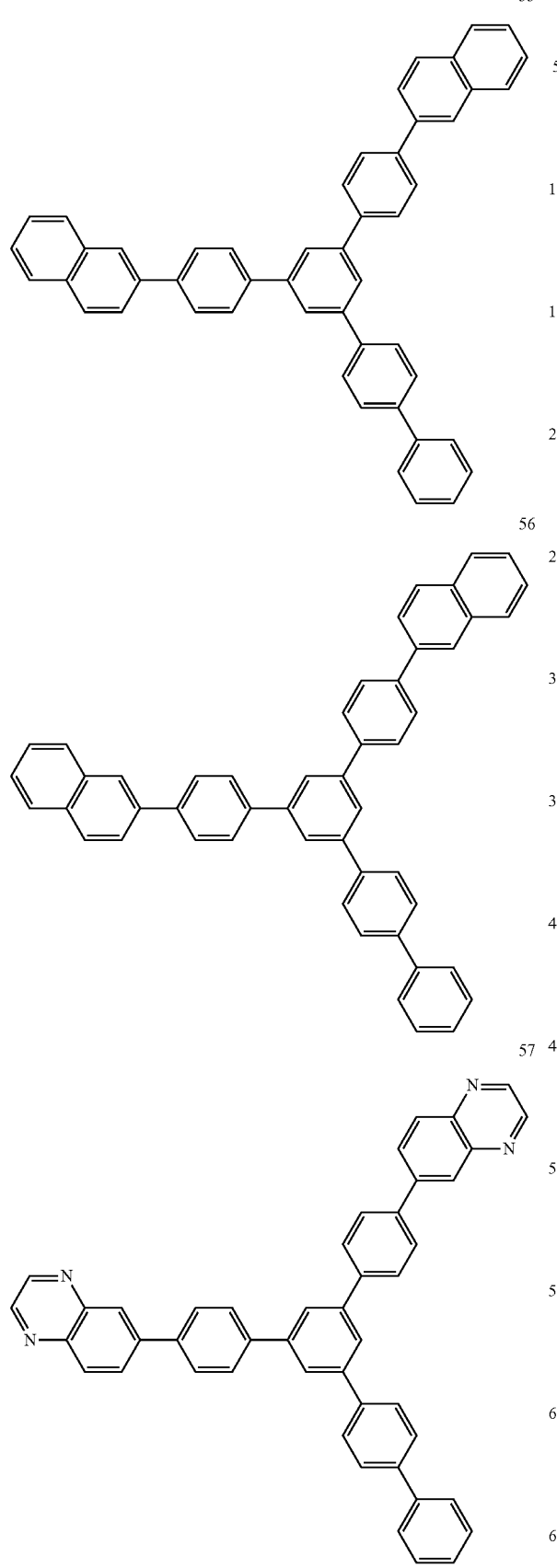
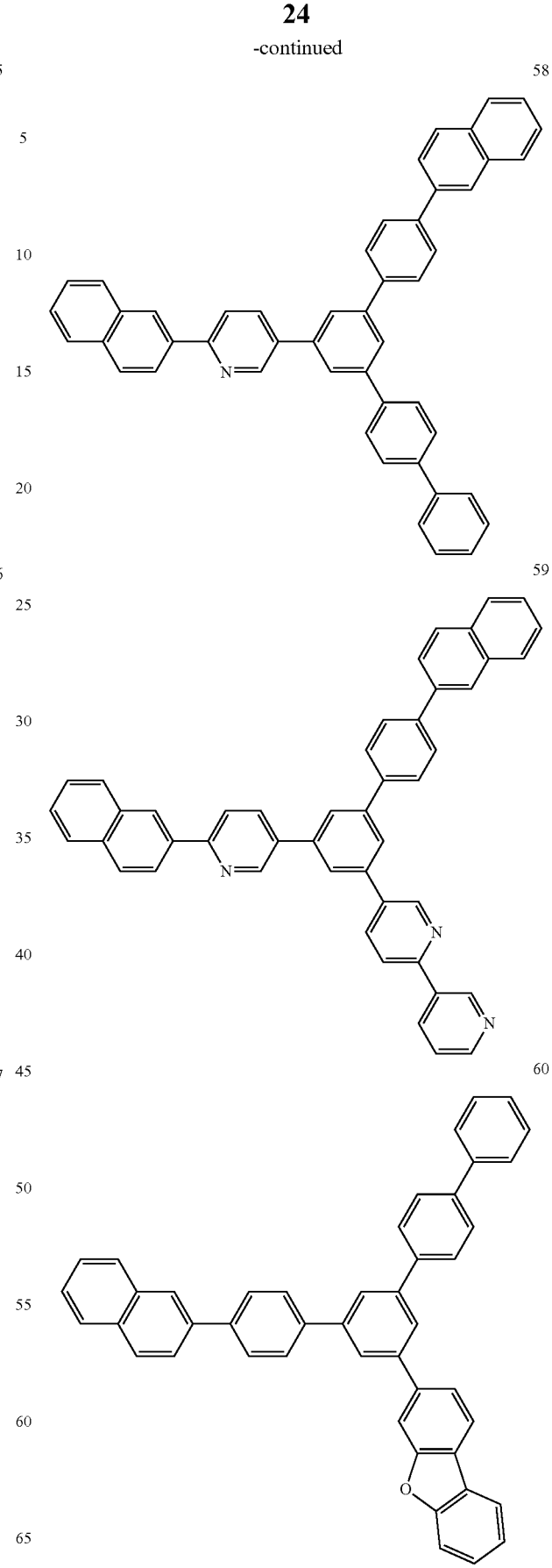

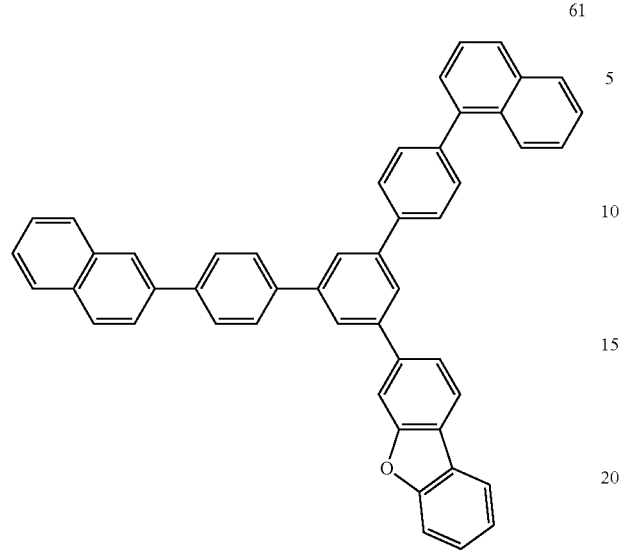
61
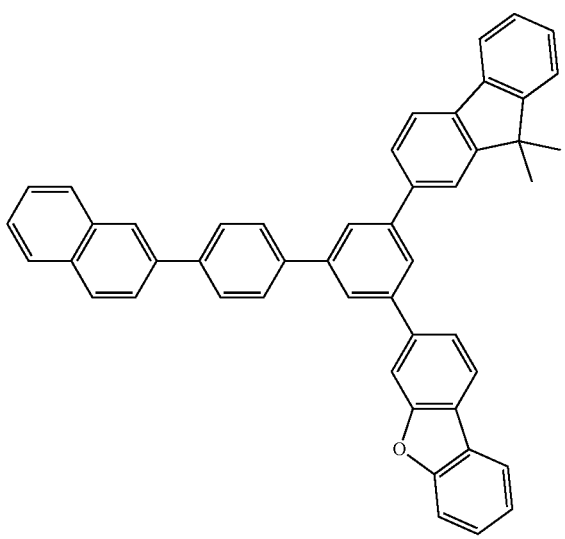
64
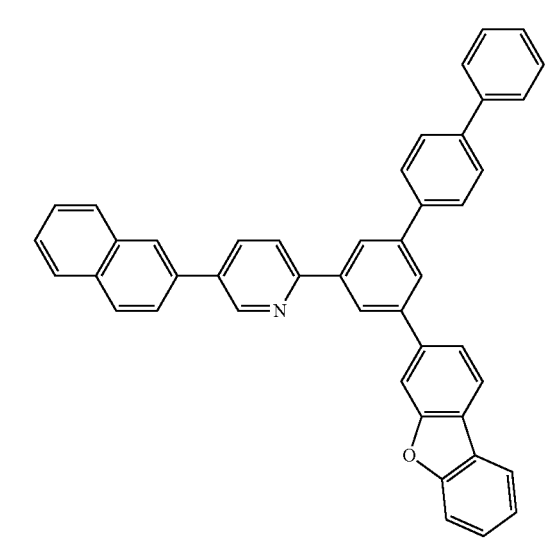
62
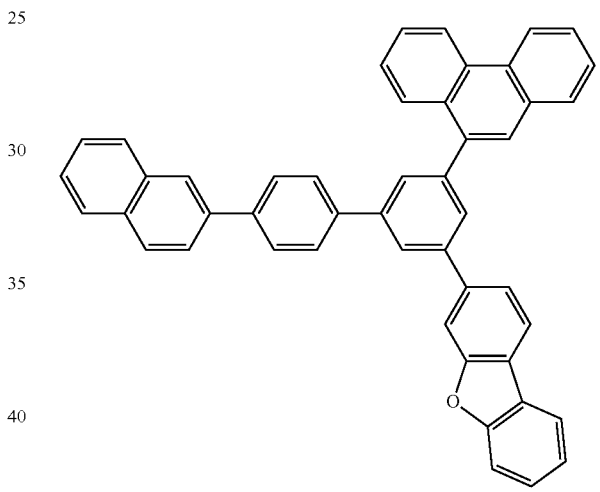
65
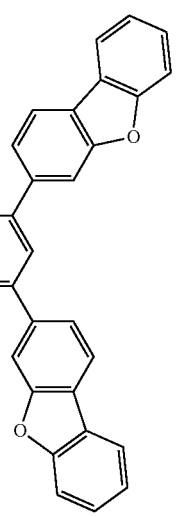
63
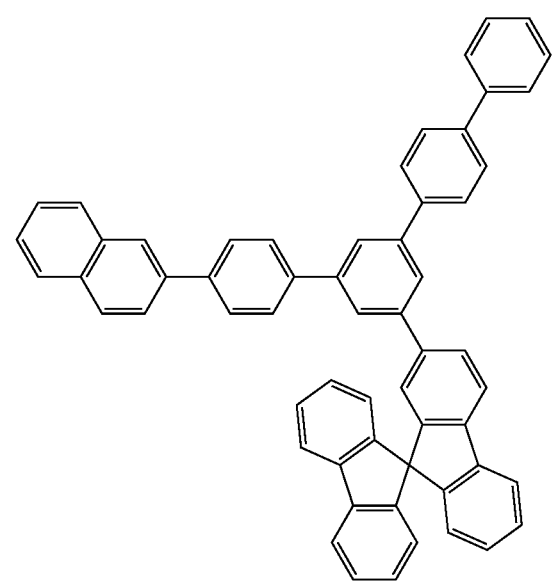
66

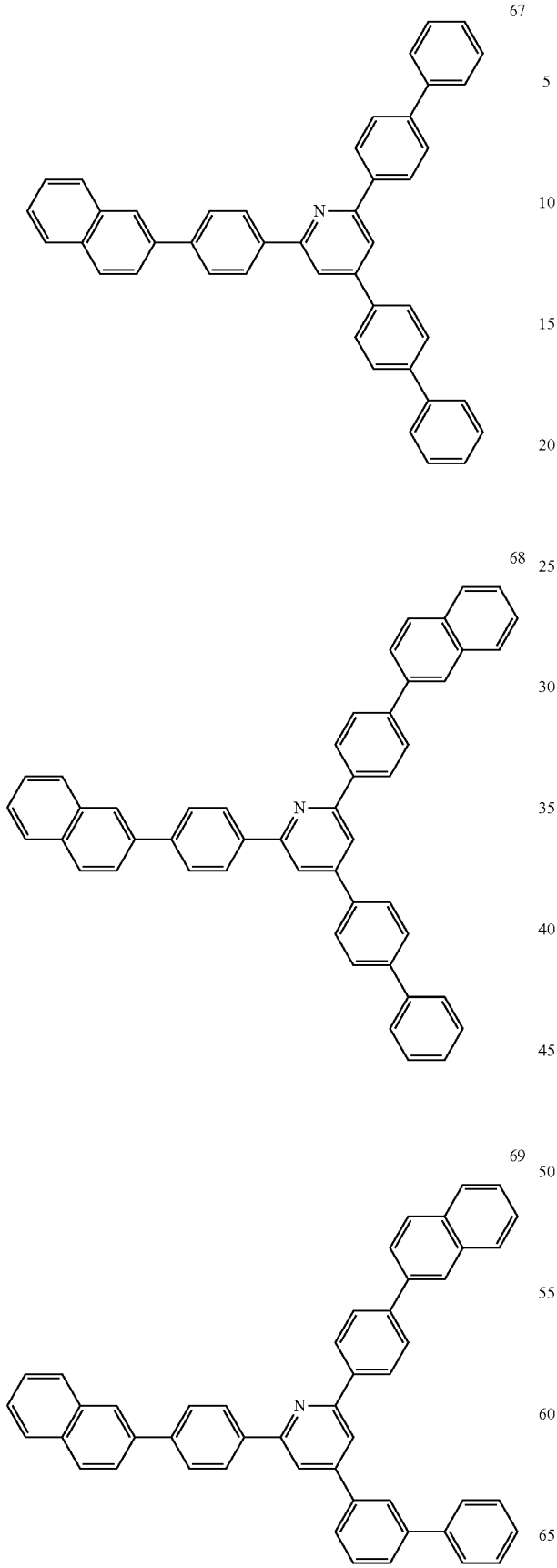
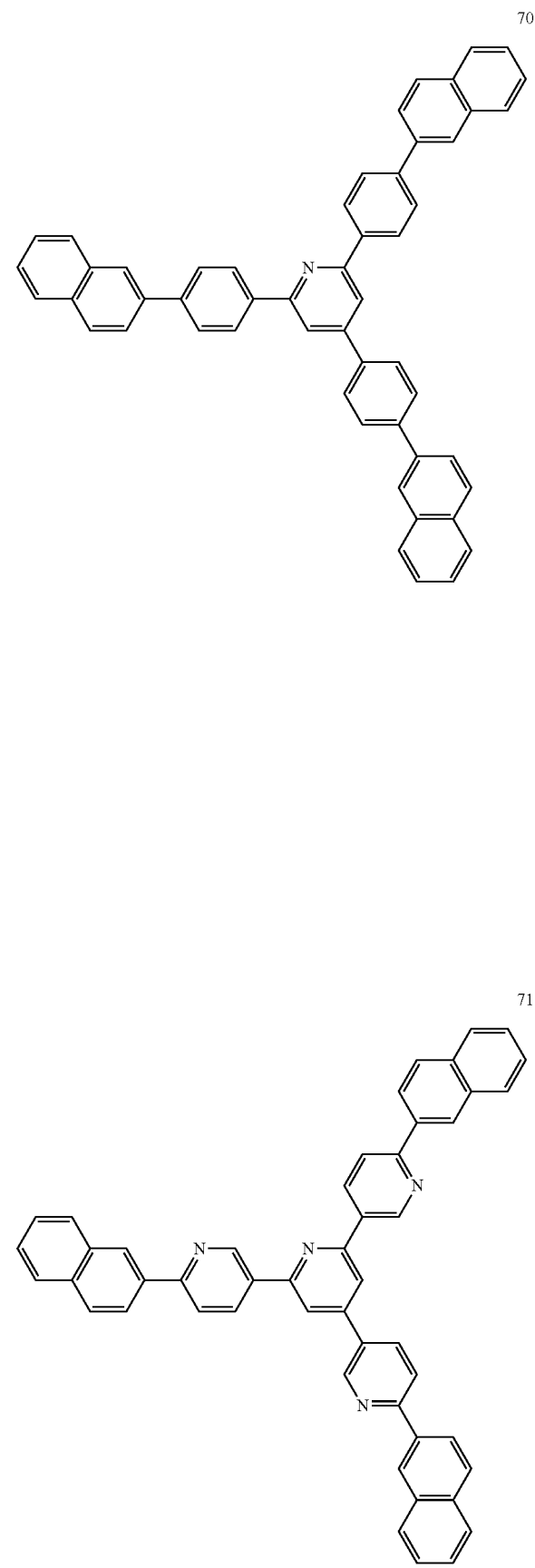

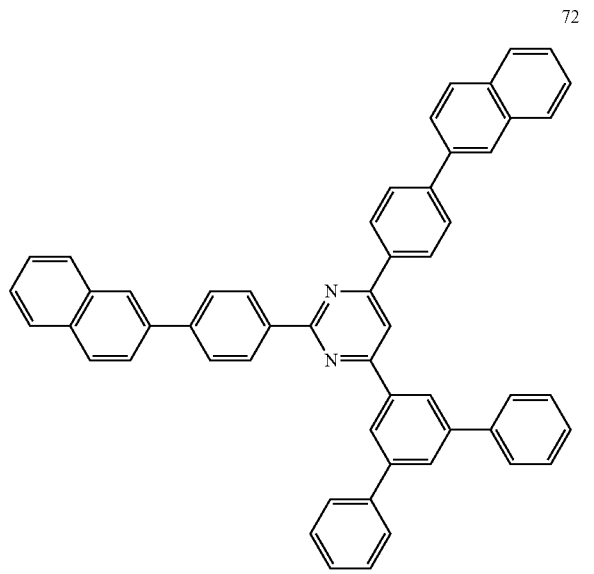
72
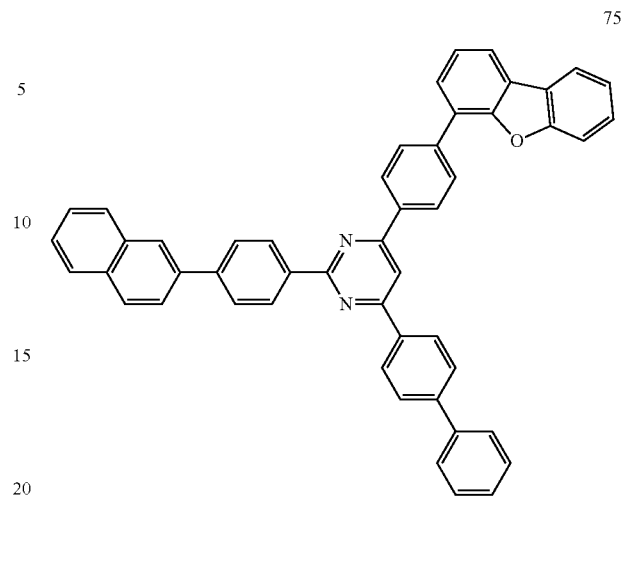
75
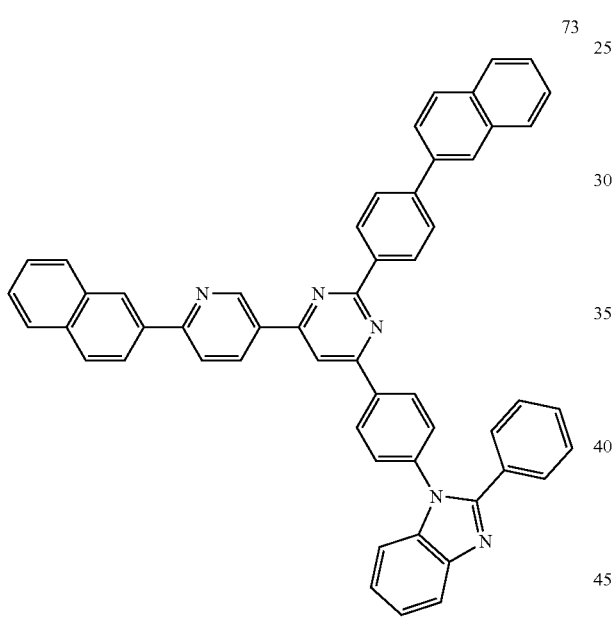
73
76
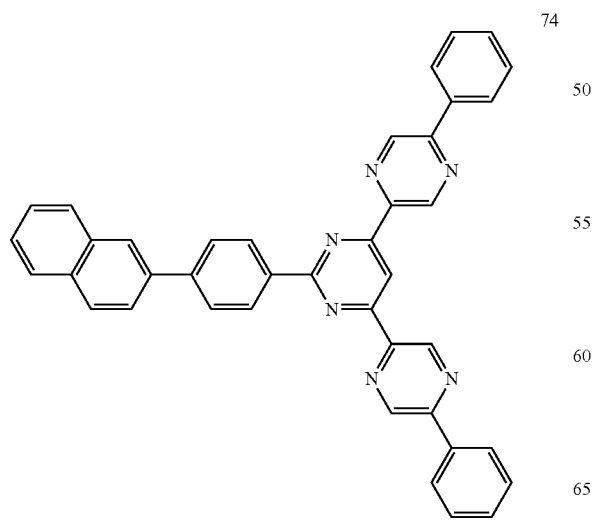
74
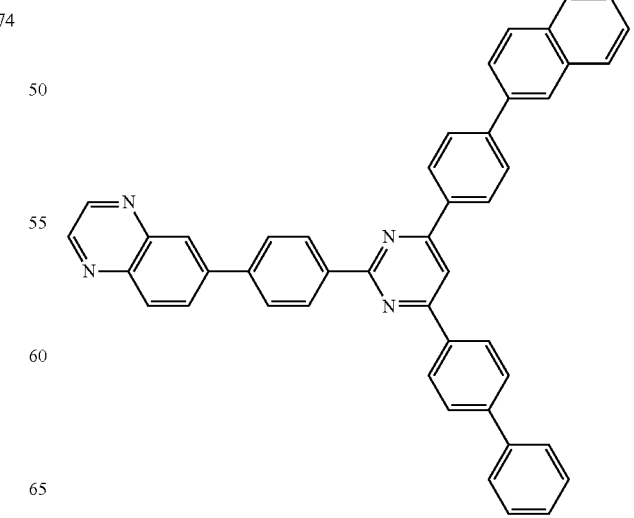
77

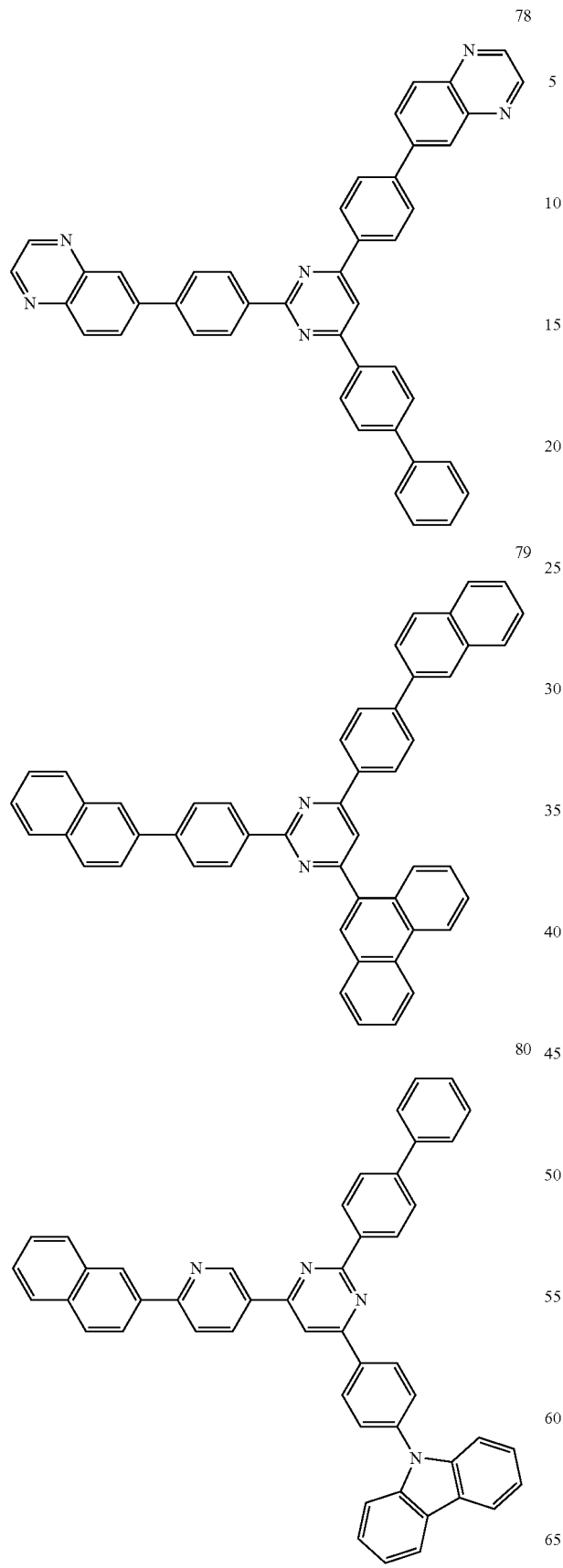
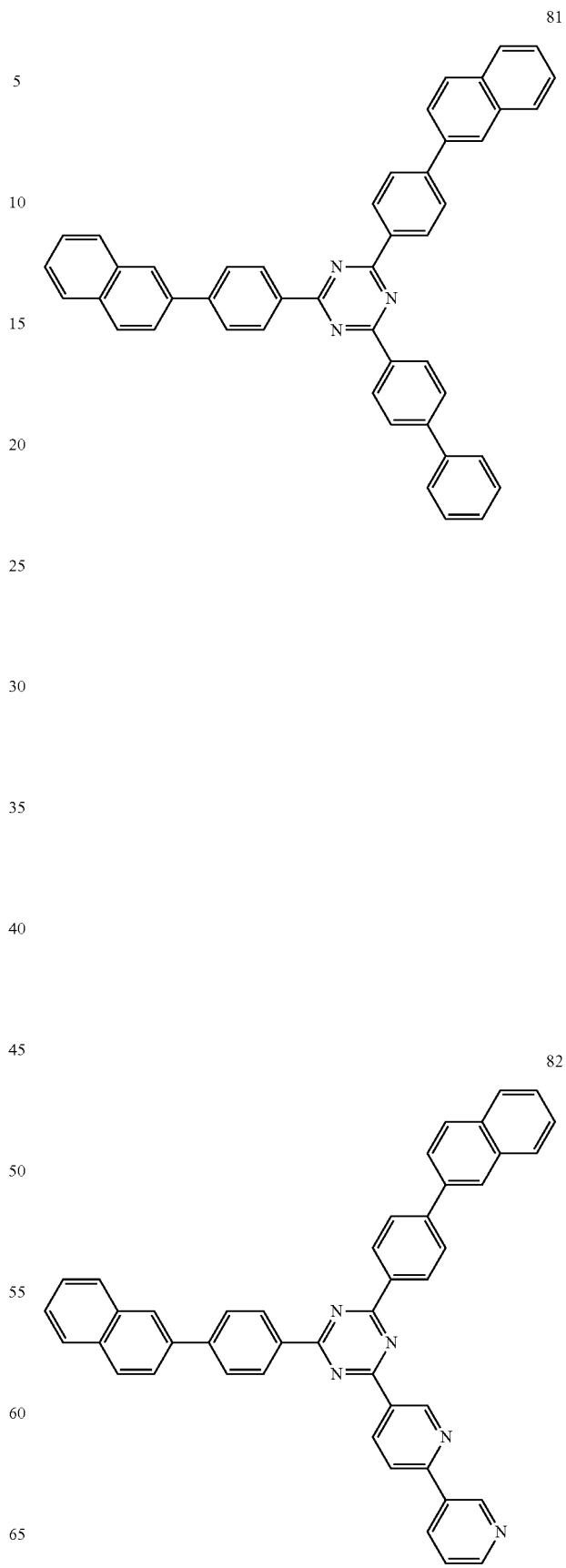

83
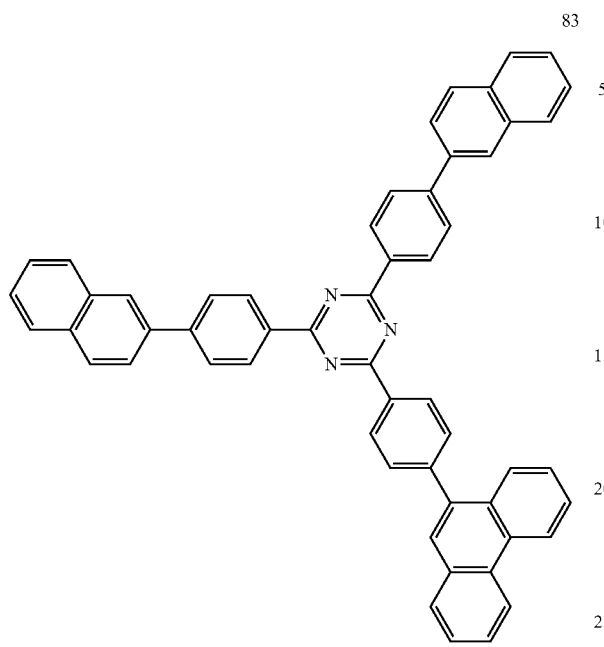
84
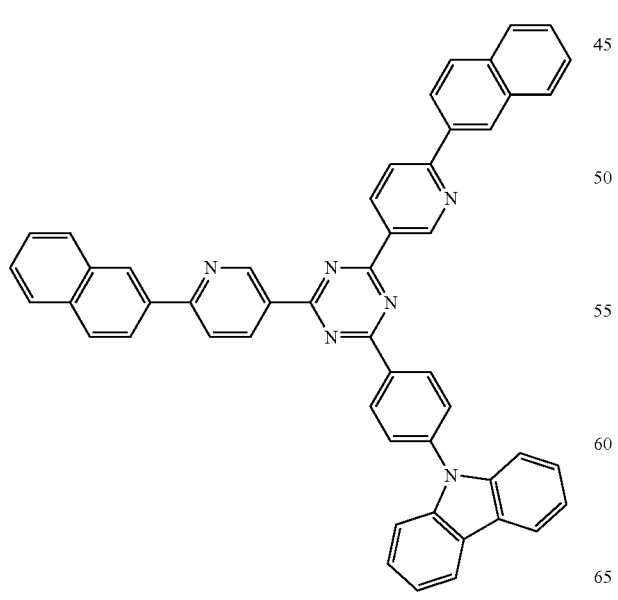
85
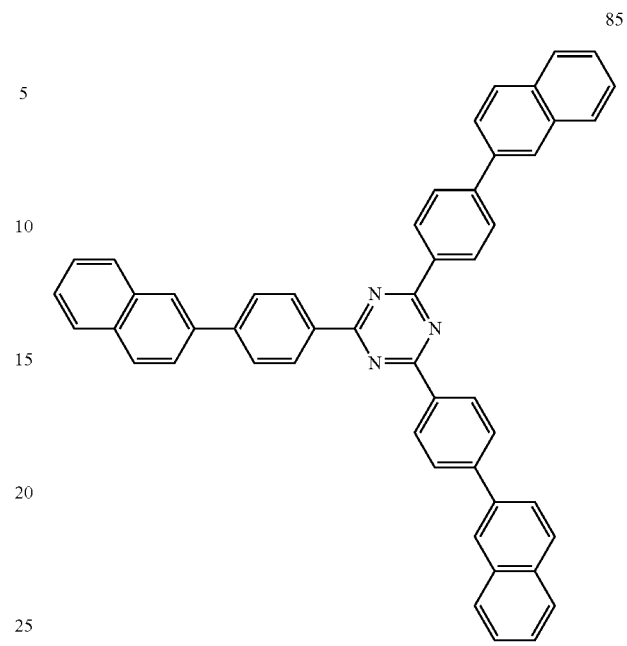
86
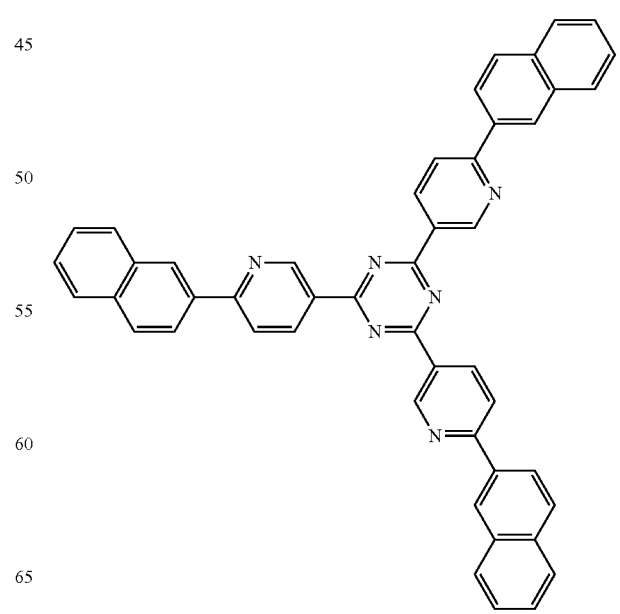

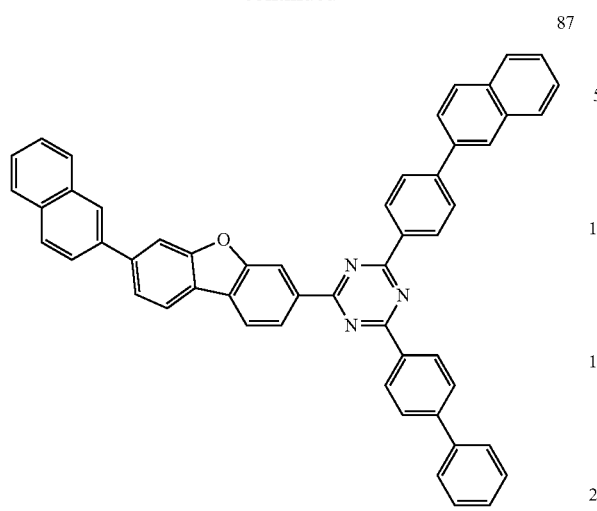
87
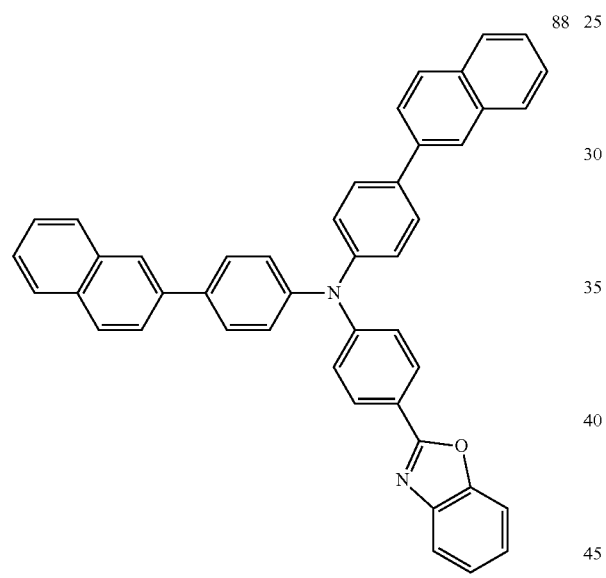
88
89
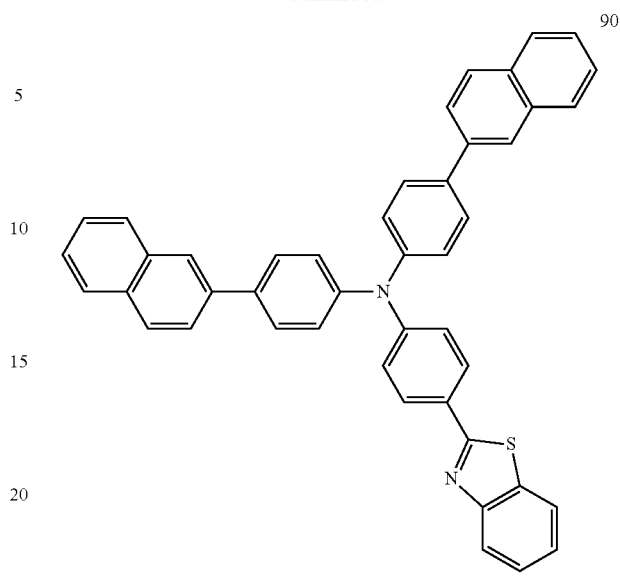
90
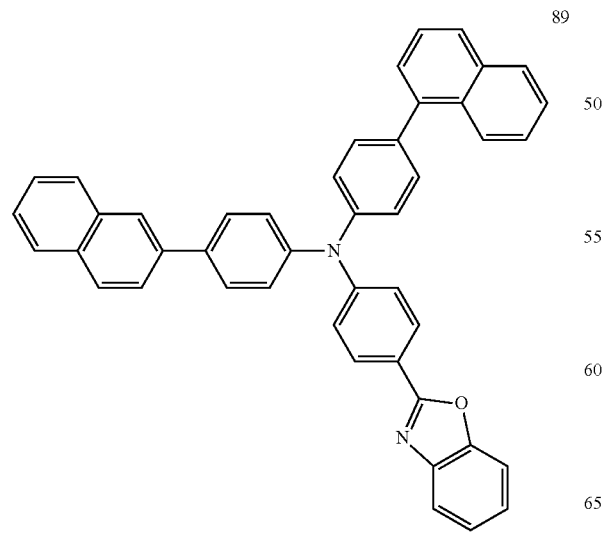
91
92

37
-continued
93
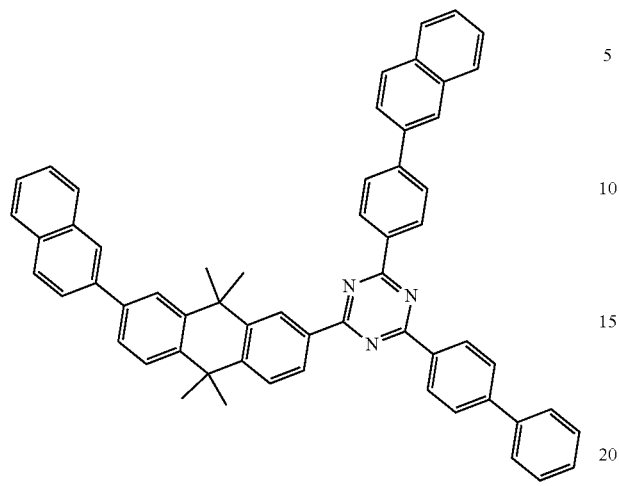
94
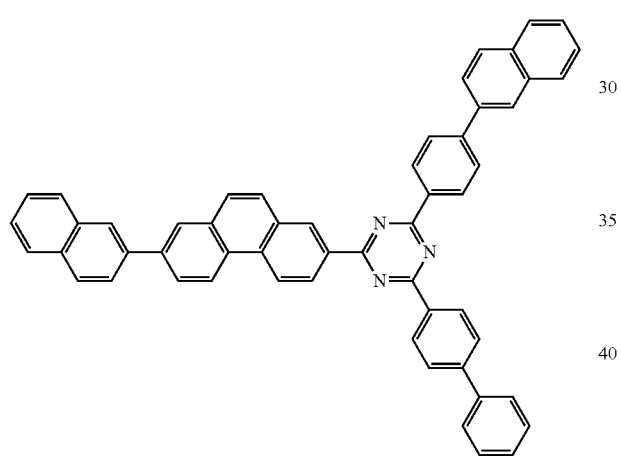
95
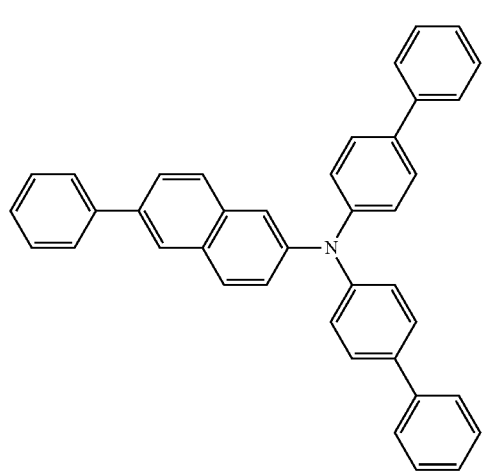
38
-continued
96
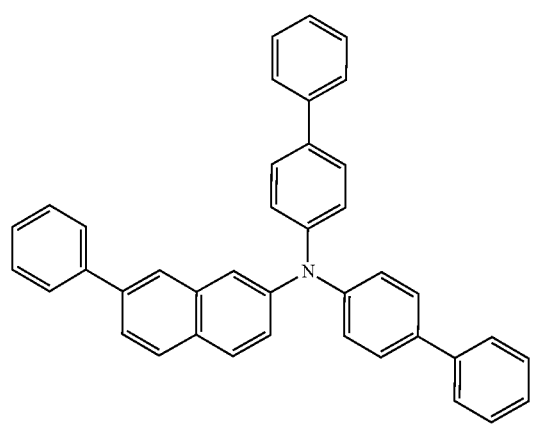
97
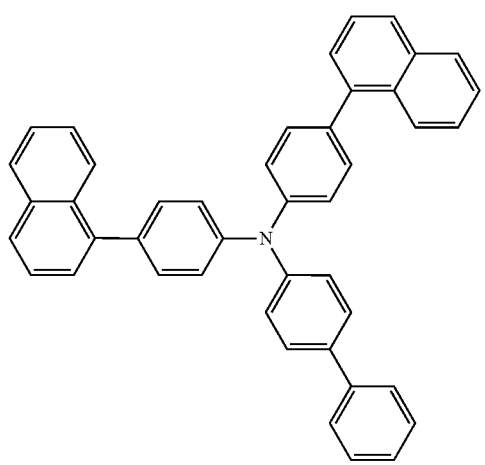
98
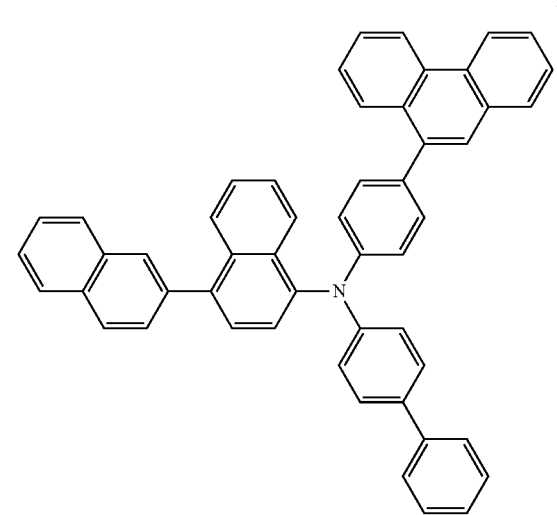

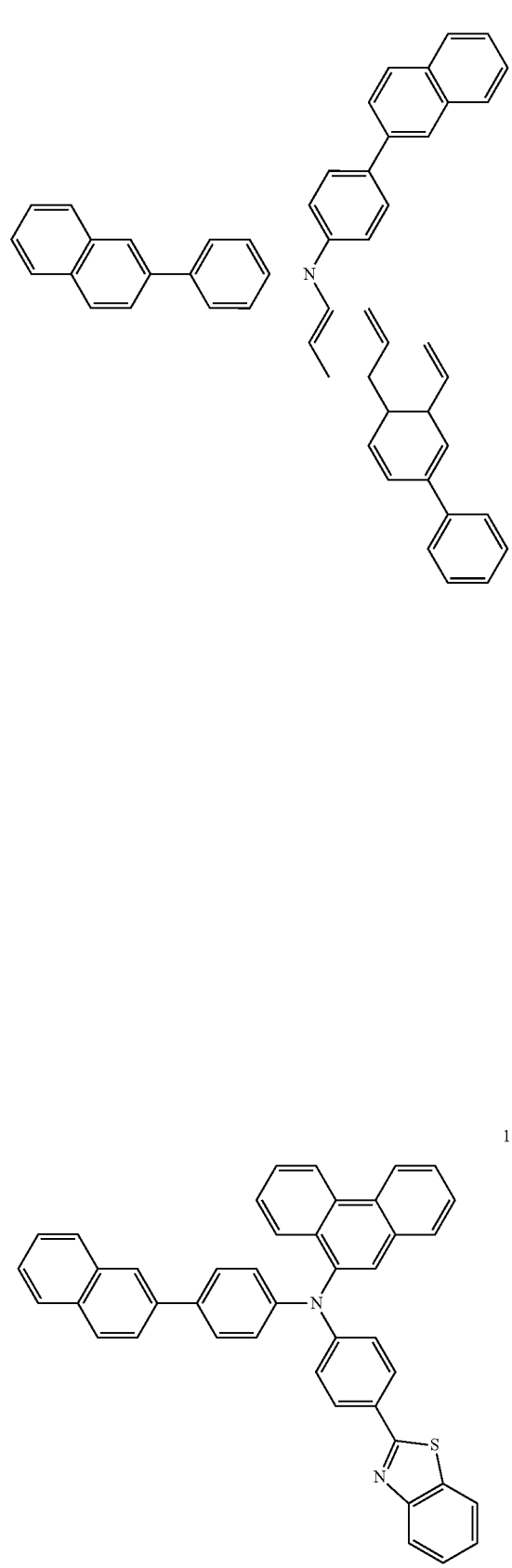
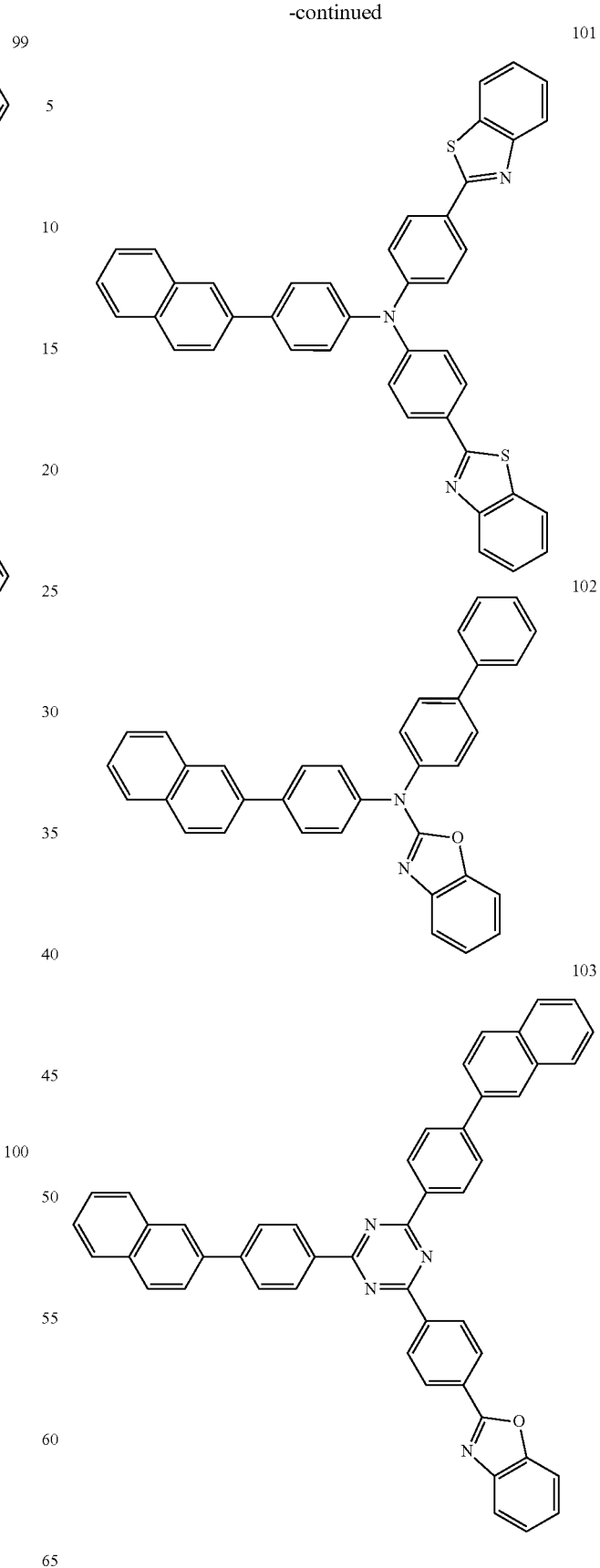
As mentioned above, the EL compound of the present disclosure has specific properties due to the structure and substituents. For example, by substituting substituents, which is included in a hole injection material, a hole transporting material, an emitting material or an electron transporting material, to the EL compound of the present disclosure, the EL compound may provide desired properties. Particularly, the EL compound may be used to the hole transporting material with or without other compound. In addition, the EL compound may be used to the light-efficiency enhancing layer, which may be referred to as a capping layer (CPL).

The EL compound may be applied to the EL device by a conventional method.

The EL device according to an exemplary embodiment may have a structure including a first electrode, a second electrode and an organic material layer therebetween. The conventional fabricating method and materials except the EL compound for the organic material layer may be used to for the EL device.

The organic material layer of the EL device may have a single-layered structure or a multi-layered structure including at least two layers. For example, the organic material layer may include a hole injection layer (HIL), a hole transporting layer (HTL), an emitting material layer (EML), an electron transporting layer (ETL) and an electron injection layer (EIL), but it is not limited thereto. The organic material layer may further include at least one of an electron blocking layer (EBL) and a hole blocking layer (HBL). The organic material layer may include less or more layers than the above multi-layered structure.

Accordingly, in the EL device of the present disclosure, the organic material layer may include at least one of the hole transporting layer and a hole injection-transporting layer, and at least one of the hole transporting layer and the hole injection-transporting layer may include the EL compound of Formula 1 or Formula 2.

The EL device may include a substrate, a first electrode as an anode, an organic material layer, a second electrode as a cathode and a light-efficiency enhancing layer. The light-efficiency enhancing layer may be formed on a lower surface of the first electrode in the bottom-emission type EL device or may be formed on an upper surface of the second electrode in the top-emission type EL device.

In the top-emission type EL device, the light from the emitting material layer is emitted through the cathode, i.e., the second electrode and passes through the light-efficiency enhancing layer, i.e., the capping layer (CPL), which includes the compound of the present disclosure having relatively high refractive index, such that the wavelength of the light is amplified (increased) and the light efficiency is improved. In addition, in the bottom-emission type EL device, the light-efficiency enhancing layer includes the compound of the present disclosure such that the light efficiency is improved by the same principle.

The structure of the organic material layer of the EL device will be further explained in more detail.

The EL device may be fabricated by forming the anode by depositing a metal, a metal oxide having conductivity or their alloy on a substrate using a deposition method, such as sputtering, e-beam evaporation, physical vapor deposition (PVD), forming the organic material layer, which includes the hole injection layer, the hole transporting layer, the emitting material layer and the electron transporting layer on the anode, and depositing a material, which is capable of serving as the cathode, on the organic material layer.

Alternatively, the EL device may be fabricated by sequentially depositing the cathode material, the organic material and the anode material. The organic material layer may be the multi-layered structure including the hole injection layer, the hole transporting layer, the emitting material layer and the electron transporting layer, but it is not limited thereto. The organic material layer may be the single-layered structure. In addition, the organic material layer may be formed by a solution process, e.g., a spin coating process, a dip coating process, a doctor blading process, a screen printing process, an inkjet printing process or a thermal transferring process.

The material for the anode may have relatively high work function to facilitate the hole injection into the organic material layer. For example, the material for the anode may be a metal, such as vanadium, chromium, copper, zinc or gold, their alloy, a metal oxide, such as zinc oxide, indium oxide, indium-tin-oxide (ITO) or indium-zinc oxide (IZO), a combination of metal and metal oxide, such as ZnO:Al or $SnO_2$:Sb, and a conductive polymer, such as poly(3-methylthiophene), poly[3,4-(ethylene-1,2-dioxy)thiophene] (PEDT), polypyrrole or polyaniline, but it is not limited thereto.

The material for the cathode may have relatively low work function to facilitate the electron injection into the organic material layer. For example, the material for the cathode may be a metal, such as magnesium, calcium, sodium, potassium, titanium, indium, yttrium, lithium, gadolinium, aluminum, silver, tin, or lead, their alloy, or a multi-structure material, such as LiF/Al or $LiO_2$/Al, but it is not limited thereto.

The hole injection material efficiently receiving the hole from the anode with low voltage is used for the hole injection layer. The highest occupied molecular orbital (HOMO) of the hole injection material is between the work function of the anode and the HOMO of adjacent organic material layer. For example, the hole injection material may be metal porphyrine, oligothiophene, arylamine-based organic material, hexa-nitrile hexaazatriphenylene, quinacridone-based organic material, perylene-based organic material, anthraquinone, polyaniline-based conductive polymer or polythiophene-based conductive polyer, but it is not limited thereto.

The hole transporting material receiving the hole from the hole injection layer or the anode and providing the hole into the emitting material layer is used for the hole transporting layer. Namely, the hole transporting material has high hole mobility. For example, the hole transporting material may be arylamine-based organic material, conductive polymer, block-co-polymer including a conjugated part and a non-conjugated part or the compound of the present disclosure. Particularly, the hole transporting layer includes the compound of the present disclosure such that the properties, e.g., the driving voltage, the emitting efficiency and the lifespan, of the EL device are further improved.

The emitting material combining the hole and electrons respectively from the hole transporting layer and the electron transporting layer and emitting visible light is used for the emitting material layer. The emitting material may be a fluorescent compound or a phosphorescent compound. For example, the emitting material may be 8-hydroxy-quinoline-aluminum complex (Alq3), carbazole-based compound, dimerized styryl compound, BAlq, 10-hydroxy-benzoquinoline metal compound, benzoxazole-based compound, benzthiazole-based compound, benzimidazole-based compound, poly(p-phenylvinylene)-based polymer, spiro-compound, polyfluorene or rubrene, but it is not limited thereto.

The electron transporting material efficiently providing the electron from the cathode into the emitting material layer is used for the electron transporting layer. Namely, the electron transporting material has high electron mobility. For example, the electron transporting material may be Alq3, organic radical compound or hydroxyflavone-metal complex, but it is not limited thereto.

The EL device of the present disclosure may be a top-emission type, a bottom-emission type or a dual-emission type depending on materials in the EL device.

In addition, the EL compound of the present disclosure may be used for an organic electronic device, such as an organic solar cell, an organic photo conductor or an organic transistor, with the same principle for the EL device.

1. Synthesis of Compound 3

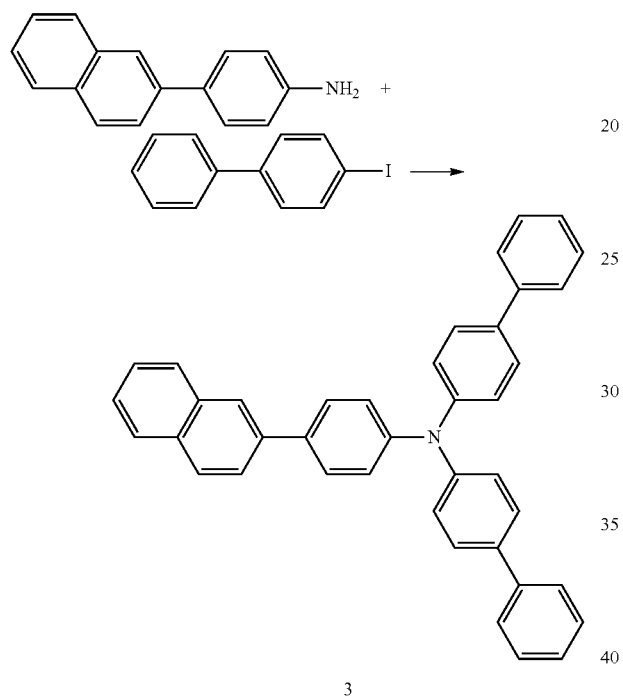

3

Toluene (300 mL) was added into a mixture of 4-(naphthalen-2-yl)aniline (10 g, 0.045 mol, Mascot), 4-iodobiphenyl (26.82 g, 0.95 mol, sigma aldrich), sodium tert-butoxide (17.53 g, 0.18 mol, sigma aldrich), Pd(dba)$_2$ (1.31 g, 0.0023 mol, sigma aldrich) as catalyst and tri-tert-Bu-phosphine (0.92 g, 0.0046 mol, sigma aldrich) and was stirred under the temperature of 100° C. for 4 hrs. After completion of reaction, by extracting and column-refining the mixture, the compound 3 (18 g, yield: 75.3%) was obtained.

H-NMR (200 MHz, CDCl$_3$):δppm, 1H(7.92/d, 7.73/d, 7.58/s) 2H(8.00/d, 7.59/m, 7.41/m) 4H(7.52/d, 7.51/m) 6H(7.54/d, 6.69/d), LC/MS: m/z=523[(M+1)+]

2. Synthesis of Compound 9

(1) Compound 9-1

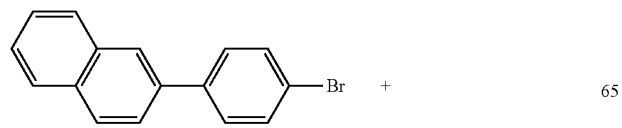

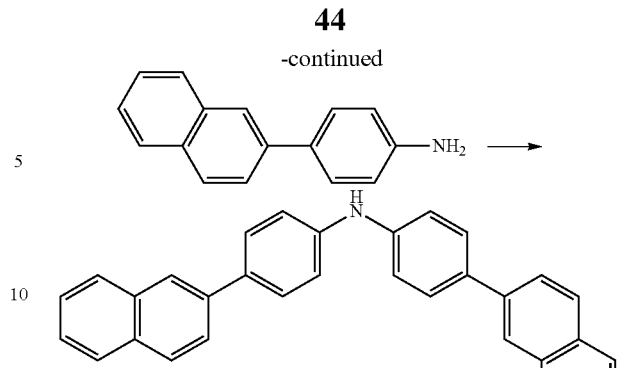

9-1

Toluene (300 mL) was added into a mixture of 2-(4-bromophenyl)naphthalene (10 g, 0.045 mol, TCI), 4-(naphthalen-2-yl)aniline (14.05 g, 0.050 mol, Mascot), sodium tert-butoxide (8.77 g, 0.091 mol, sigma aldrich), Pd(dba)$_2$ (1.31 g, 0.0023 mol, sigma aldrich) and tri-tert-Bu-phosphine (0.92 g, 0.0046 mol, sigma aldrich) and was stirred under the temperature of 100° C. for 4 hrs. After completion of reaction, by extracting and column-refining the mixture, the compound 9-1 (14.4 g, yield: 74.9%) was obtained.

(2) Compound 9

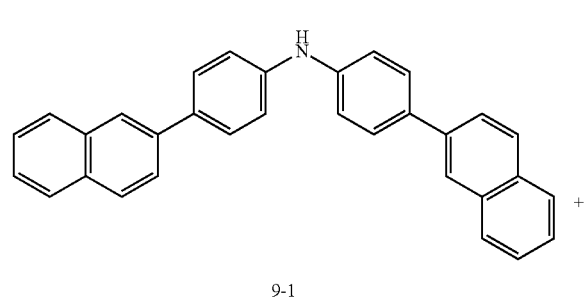

9-1

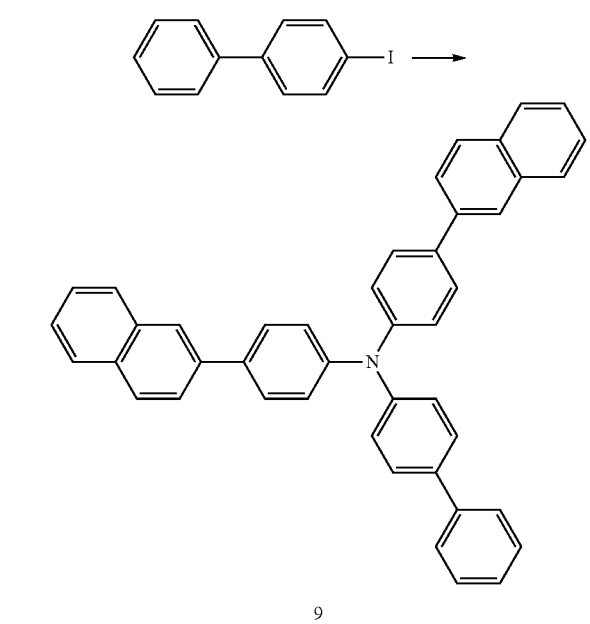

9

Toluene (200 mL) was added into a mixture of the compound 9-1 (10 g, 0.023 mol), 4-iodobiphenyl (7.31 g, 0.026 mol, sigma aldrich), sodium tert-butoxide (4.56 g, 0.047 mol, sigma aldrich), Pd(dba)$_2$ (0.68 g, 0.0012 mol, sigma aldrich) and tri-tert-Bu-phosphine (0.48 g, 0.0024 mol, sigma aldrich) and was stirred under the temperature of 100° C. for 5 hrs. After completion of reaction, by extracting and column-refining the mixture, the compound 9 (10.2 g, yield: 74.9%) was obtained.

H-NMR (200 MHz, CDCl$_3$):δppm, 1H(7.41/m) 2H(7.92/d, 7.73/d, 7.58/d, 7.52/d, 7.51/m) 4H(8.00/d, 7.59/m) 6H(7.54/d, 6.69/d), LC/MS: m/z=573[(M+1)$^+$]

3. Synthesis of Compound 18

(1) Compound 18-1

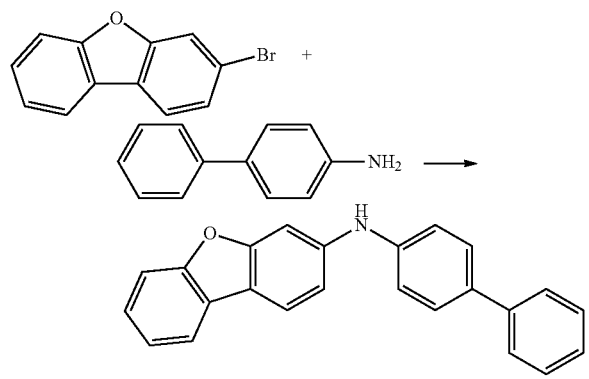

18-1

Toluene (300 mL) was added into a mixture of 3-bromodibenzofuran (20 g, 0.081 mol, TCI), 4-aminobiphenyl (16.44 g, 0.097 mol, sigma aldrich), sodium tert-butoxide (15.56 g, 0.16 mol, sigma aldrich), Pd(dba)$_2$ (2.33 g, 0.004 mol, sigma aldrich) and tri-tert-Bu-phosphine (1.64 g, 0.008 mol, sigma aldrich) and was stirred under the temperature of 100° C. for 3 hrs. After completion of reaction, by extracting and column-refining the mixture, the compound 18-1 (19.2 g, yield: 70.7%) was obtained.

(2) Compound 18

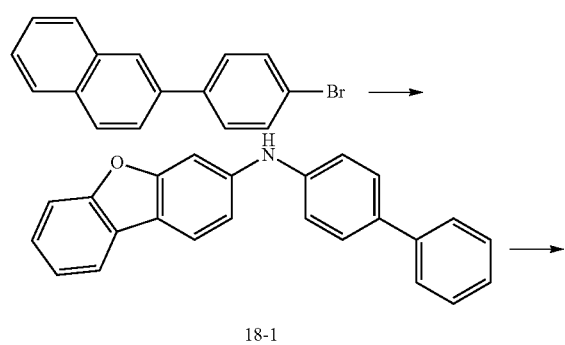

18-1

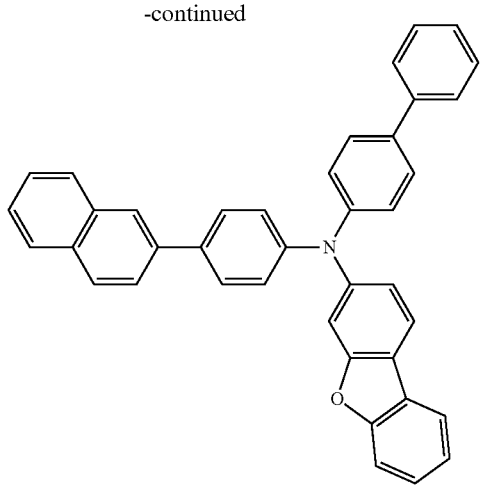

18

Toluene (150 mL) was added into a mixture of 2-(4-bromophenyl)naphthalene (10 g, 0.035 mol, TCI), the compound 18-1 (13.03 g, 0.038 mol), sodium tert-butoxide (6.79 g, 0.070 mol, sigma aldrich), Pd(dba)$_2$ (1.02 g, 0.0018 mol, sigma aldrich) and tri-tert-Bu-phosphine (0.71 g, 0.0035 mol, sigma aldrich) and was stirred under the temperature of 100° C. for 12 hrs. After completion of reaction, by extracting and column-refining the mixture, the compound 18 (14.4 g, yield: 75.8%) was obtained.

H-NMR (200 MHz, CDCl$_3$):δppm, 1H(7.92/d, 7.89/d, 7.73/d, 7.66/d, 7.64/d, 7.58/s, 7.43/s, 7.41/m, 7.38/m, 7.32/m, 6.33/d) 2H(8.00/d, 7.59/m, 7.52/d, 7.51/m) 4H(7.54/d, 6.69/d), LC/MS: m/z=537[(M+1)$^+$]

4. Synthesis of Compound 51

(1) Compound 51-1

51-1

Toluene (150 mL) was added into a mixture of 4-bromobiphenyl (10 g, 0.040 mol, sigma aldrich), 4-aminobiphenyl (7.53 g, 0.044 mol, sigma aldrich), sodium tert-butoxide (7.78 g, 0.081 mol, sigma aldrich), Pd(dba)$_2$ (1.16 g, 0.002 mol, sigma aldrich) and tri-tert-Bu-phosphine (0.82 g, 0.004 mol, sigma aldrich) and was stirred under the temperature of 100° C. for 5 hrs. After completion of reaction, by extracting and column-refining the mixture, the compound 51-1 (10.5 g, yield: 80.7%) was obtained.

(2) Compound 51-2

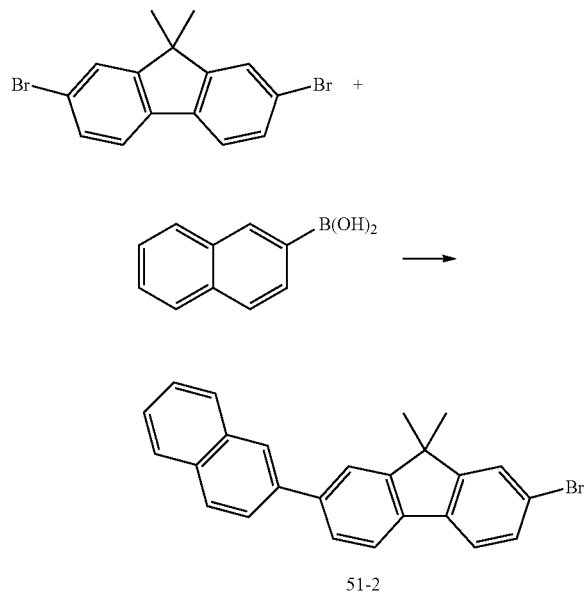

Toluene (150 mL) and water (40 mL) were added into a mixture of 2,7-dibromo-9,9-dimethyl-9H-fluorene (10 g, 0.039 mol, sigma aldrich), 2-naphthylboronic acid (7.51 g, 0.047 mol, sigma aldrich), potassium carbonate (16.45 g, 0.12 mol, sigma aldrich) and Pd(PPh$_3$)$_4$ (2.29 g, 0.002 mol, sigma aldrich) and was stirred under the temperature of 60° C. for 4 hrs. After completion of reaction, by extracting and column-refining the mixture, the compound 51-2 (12 g, yield: 75.7%) was obtained.

(3) Compound 51

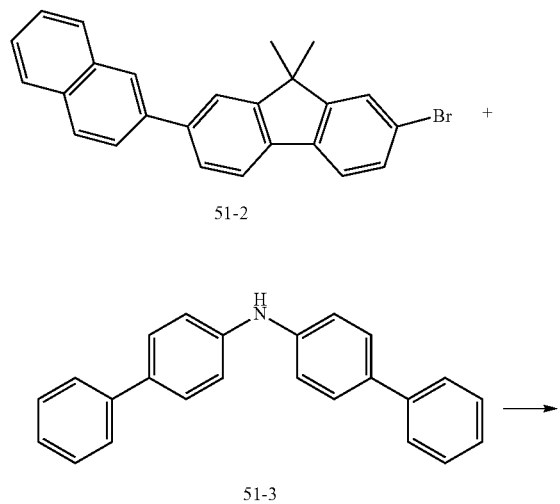

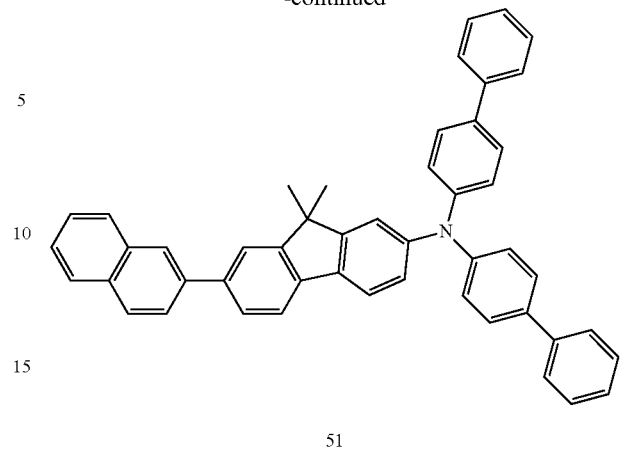

Toluene (150 mL) was added into a mixture of the compound 51-2 (10 g, 0.025 mol), the compound 51-1 (8.85 g, 0.027 mol), sodium tert-butoxide (4.81 g, 0.050 mol, sigma aldrich), Pd(dba)$_2$ (0.72 g, 0.0013 mol, sigma aldrich) and tri-tert-Bu-phosphine (0.51 g, 0.0025 mol, sigma aldrich) and was stirred under the temperature of 100° C. for 12 hrs. After completion of reaction, by extracting and column-refining the mixture, the compound 51 (12 g, yield: 74.8%) was obtained.

H-NMR (200 MHz, CDCl$_3$):δppm, 1H(7.93/d, 7.92/d, 7.77/s, 7.73/d, 7.63/d, 7.62/d, 7.58/s, 6.75/s, 6.58/d) 2H(8.00/d, 7.59/m, 7.41/m) 3H(6H(1.72/s) 4H(7.54/d, 7.52/d, 7.51/m, 6.69/d) 6H(1.72/s), LC/MS: m/z=639[(M+1)$^+$]

5. Synthesis of Compound 71

(1) Compound 71-1

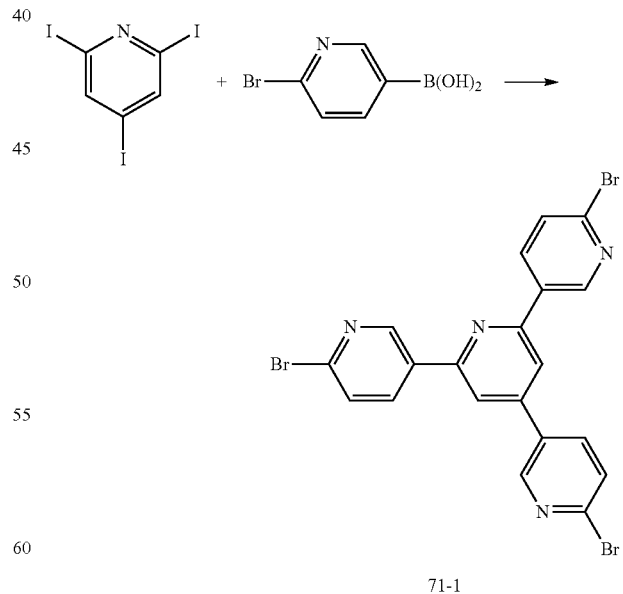

Toluene (200 mL) and water (50 mL) were added into a mixture of 2,4,6-triiodopyridine (10 g, 0.028 mol, Mascot), 6-bromo-3-pyridinylboronic acid (18.34 g, 0.09 mol, sigma aldrich), potassium carbonate (27.48 g, 0.0198 mol, sigma aldrich) and Pd(PPh₃)₄ (1.64 g, 0.0014 mol, sigma aldrich) and was stirred under the temperature of 60° C. for 8 hrs. After completion of reaction, by extracting and column-refining the mixture, the compound 71-1 (12 g, yield: 77.2%) was obtained.

(2) Compound 71

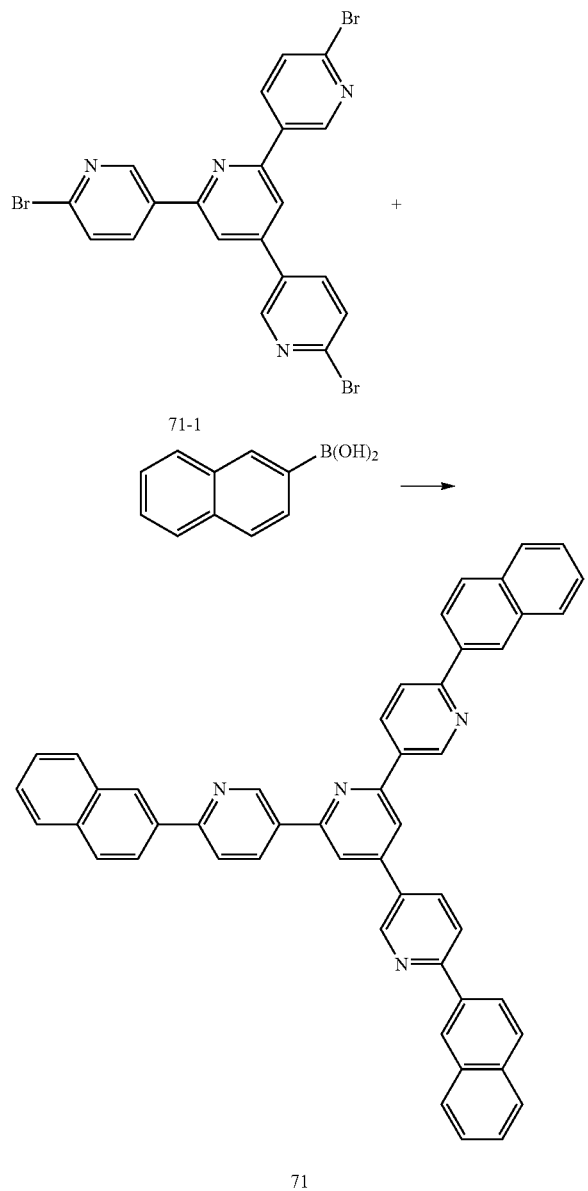

Toluene (200 mL) and water (50 mL) were added into a mixture of the compound 71-1 (10 g, 0.018 mol), 2-naphthylboronic acid (10.06 g, 0.058 mol, sigma aldrich), potassium carbonate (17.69 g, 0.128 mol, sigma aldrich) and Pd(PPh₃)₄ (1.06 g, 0.0009 mol, sigma aldrich) and was stirred under the temperature of 60° C. for 8 hrs. After completion of reaction, by extracting and column-refining the mixture, the compound 71 (9.3 g, yield: 73.8%) was obtained.

H-NMR (200 MHz, CDCl₃):δppm, 1H(8.78/s, 8.03/d, 7.69/d) 2H(9.29/s, 8.62/s, 8.20/d, 8.06/d) 3H(8.85/s, 8.38/d, 7.95/d) 6H(8.00/d, 7.59/m), LC/MS: m/z=688[(M+1)⁺]

[Device]

An ITO transparent electrode is formed on the glass substrate and patterned to have an emitting area of 2 mm*2 mm. The substrate including the ITO transparent electrode is cleaned. The substrate is loaded in the vacuum chamber of the base pressure of 1*10⁻⁶ Torr, and organic materials and a metal are deposited as below.

The compound of the present disclosure is used for the hole transporting layer, and the blue EL device having a structure of ITO; HIL (Formula 6, 5 nm), HTL (100 nm), EBL (Formula 7, 10 nm), EML (host(Formula 8):dopant (Formula 9), 20 nm), ETL (Formula 10:Lig(50 wt % doping), 30 nm), EIL (LiF, 1 nm) and Al (100 nm) is fabricated.

Examples 1 to 9 (Ex1 to Ex9)

The compounds 3, 9, 18, 23, 32, 45, 51, 93 and 95 are used to form the HTL.

Comparative Example (Ref)

The compound of Formula 11 is used to form the HTL.

[Formula 6]

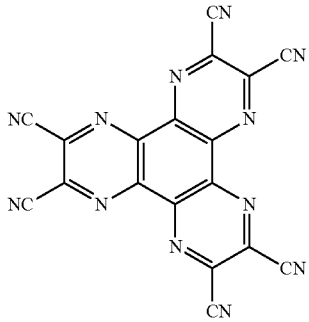

[Formula 7]

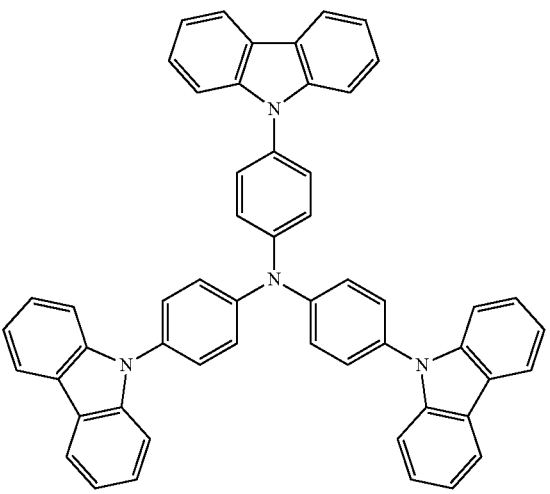

[Formula 8]

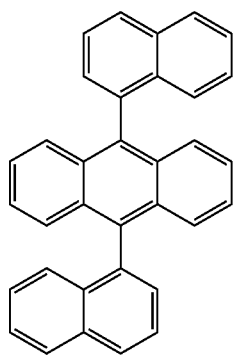

[Formula 9]

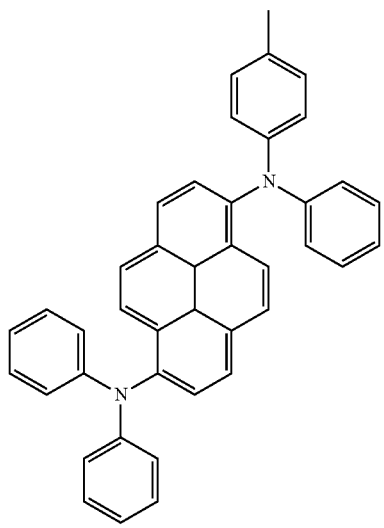

[Formula 10]

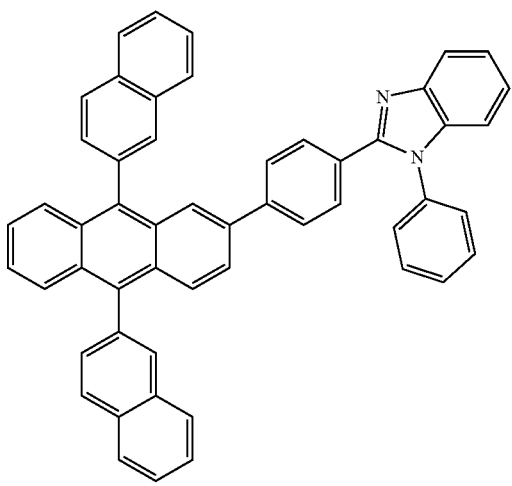

[Formula 11]

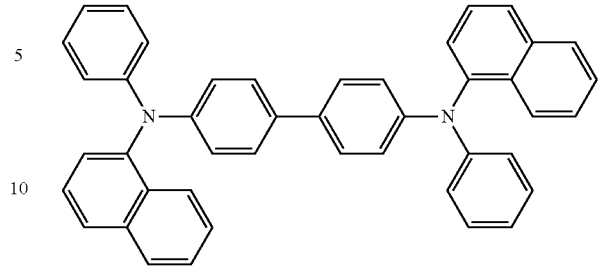

The properties, e.g., the driving voltage (V), the current efficiency (cd/A), the quantum efficiency (QE) and the color coordinate index (CIEx, CIEy), of the EL device of Examples 1 to 9 and Comparative Example are measured by the source meter (Model 237, Keithley) and the brightness meter (PR-650, Photo Research) and listed in Table 1. The voltage for the current density of 10 mA/cm$^2$ is defined as the driving voltage.

TABLE 1

|      | V    | cd/A | QE(%) | CIEx  | CIEy  |
|------|------|------|-------|-------|-------|
| Ex 1 | 3.94 | 7.87 | 6.70  | 0.144 | 0.153 |
| Ex 2 | 4.02 | 7.77 | 6.58  | 0.144 | 0.154 |
| Ex 3 | 4.13 | 7.64 | 6.42  | 0.144 | 0.155 |
| Ex 4 | 4.20 | 7.39 | 6.10  | 0.145 | 0.156 |
| Ex 5 | 4.04 | 7.78 | 6.58  | 0.144 | 0.154 |
| Ex 6 | 4.16 | 7.48 | 6.20  | 0.145 | 0.155 |
| Ex 7 | 4.22 | 7.40 | 6.12  | 0.145 | 0.155 |
| Ex 8 | 4.17 | 7.51 | 6.25  | 0.144 | 0.154 |
| Ex 9 | 4.19 | 7.45 | 6.20  | 0.145 | 0.154 |
| Ref  | 4.20 | 6.20 | 5.10  | 0.145 | 0.156 |

As shown in Table. 1, in comparison to the EL device of Comparative Example, the emitting property, e.g., emitting efficiency and the quantum efficiency, of the EL device of Examples 1 to 9, which includes the compound in the HTL, is significantly superior.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. An electroluminescent device, comprising:
   a first electrode;
   a second electrode facing the first electrode;
   at least one organic material layer between the first and second electrodes; and
   a light-efficiency enhancing layer on a side of one of the first electrode and the second electrode,
   wherein the light-efficiency enhancing layer is positioned to be opposite to the organic material layer,
   wherein the light-efficiency enhancing layer includes an electroluminescent compound of Formula 1;
   wherein one or more of the at least one organic material layer includes the electroluminescent compound of Formula 1, and wherein the electroluminescent compound of Formula 1 is:

[Formula 1]

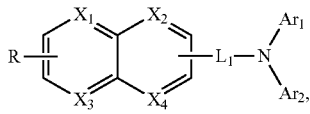

wherein each of $X_1$ to $X_4$ is independently N or CR', wherein each of R and R' is independently selected from the group consisting of hydrogen, deuterium, cyano group, hydroxyl group, halogen, a substituted or non-substituted C1 to C10 alkyl group, a substituted or non-substituted C6 to C20 aryl group and a substituted or non-substituted C3 to C30 heteroaryl group, wherein $L_1$ is selected from a single bond, a substituted or non-substituted C6 to C20 arylene group and a substituted or non-substituted C3 to C30 heteroarylene group, and wherein $Ar_1$ is a substituted or non-substituted C6 to C20 aryl group, and $Ar_2$ is a substituted or non-substituted C3 to C30 heteroaryl group.

2. The electroluminescent device according to claim 1, wherein $L_1$ is selected from Formula 3a and 3b:

[Formula 3a]

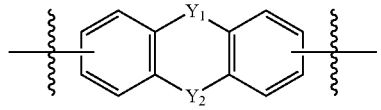

[Formula 3b]

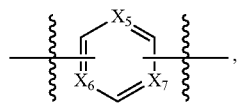

wherein each of $X_5$ to $X_7$ is independently N or $CR_1$, wherein each of $Y_1$ and $Y_2$ is independently selected from a single bond, O, S, Se, $Si(R_2)(R_4)$, and $C(R_3)(R_5)$, and wherein each of $R_1$, $R_2$, $R_3$, $R_4$ and $R_5$ is independently selected from the group consisting of hydrogen, deuterium, cyano group, hydroxyl group, halogen, a substituted or non-substituted C1 to C10 alkyl group, a substituted or non-substituted C6 to C20 aryl group and substituted or a non-substituted C3 to C30 heteroaryl group.

3. The electroluminescent device according to claim 1, wherein when substituted, each substituent of $L_1$, $Ar_1$ and $Ar_2$ is independently selected from the group consisting of deuterium, cyano group, halogen, amino group, hydroxyl group, nitro group, a substituted or non-substituted C1 to C10 alkyl group, a substituted or non-substituted C1 to C10 halogenated alkyl group, a substituted or non-substituted C6 to C20 aryl group, a substituted or non-substituted C3 to C30 heteroaryl group, a substituted or non-substituted C1 to C10 alkoxy group, a substituted or non-substituted C1 to C10 alkylsilyl group and a substituted or non-substituted C6 to C20 arylsilyl group.

4. The electroluminescent device according to claim 1, wherein the electroluminescent compound is selected from Formula 5:

[Formula 5]

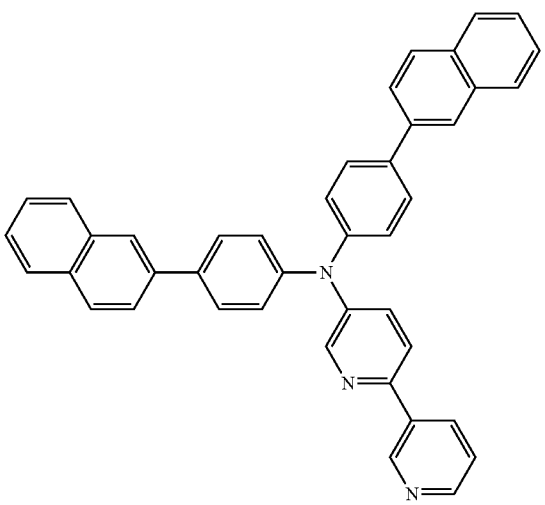

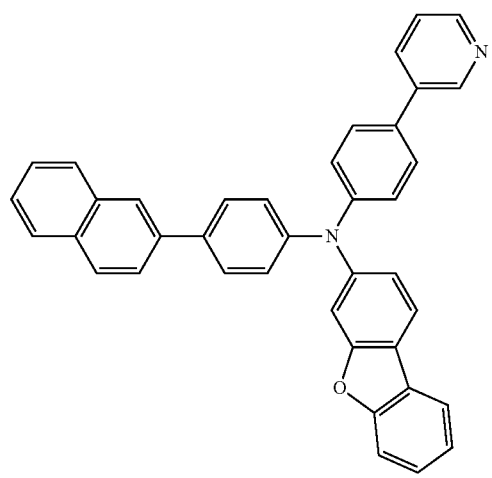
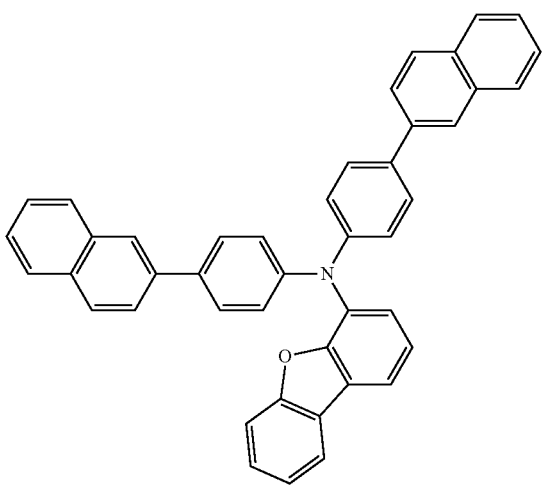

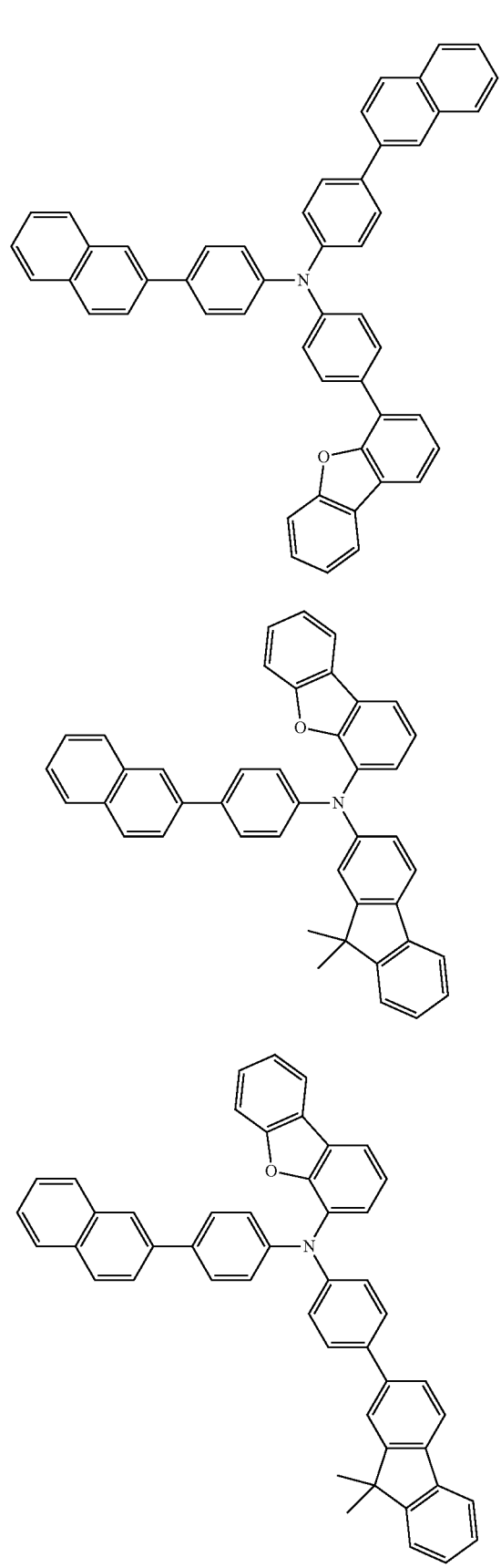
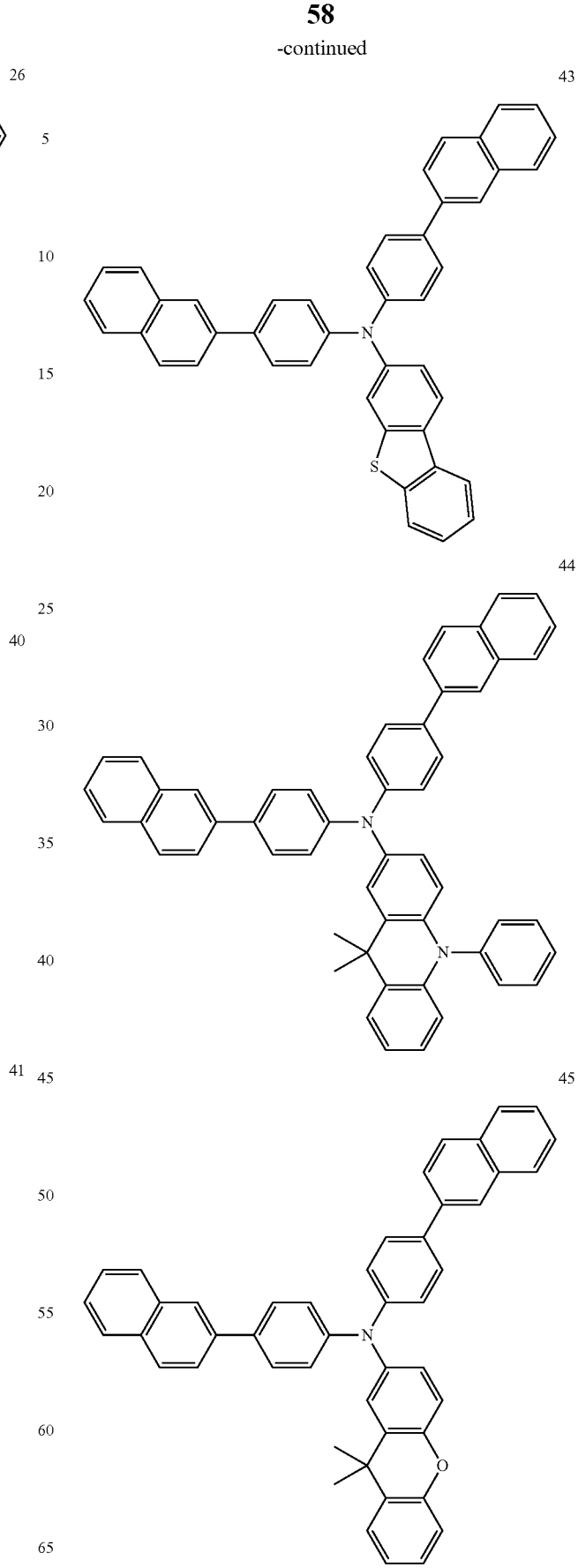

-continued

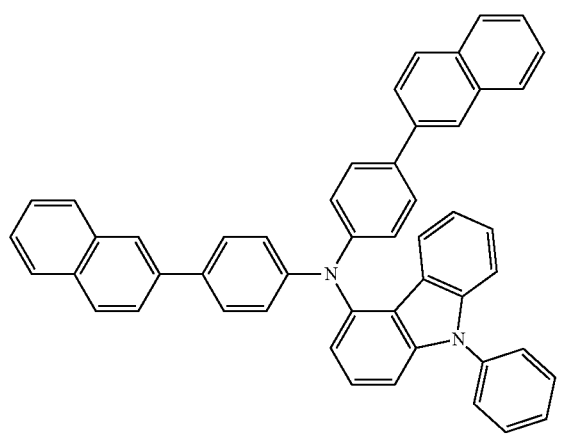

46

5. The electroluminescent device according to claim 1, wherein the at least one organic material layer includes at least one of an electron injection layer, an electron transporting layer, a hole injection layer, a hole transporting layer, an electron blocking layer, a hole blocking layer and an emitting material layer.

6. The electroluminescent device according to claim 5, wherein the hole transporting layer includes the electroluminescent compound.

7. The electroluminescent device according claim 1, wherein the light-efficiency enhancing layer is formed on at least one of a lower surface of the first electrode and an upper surface of the second electrode.

8. The electroluminescent device according to claim 1, wherein $L_1$ is selected from Formula 3a and 3b:

[Formula 3a]

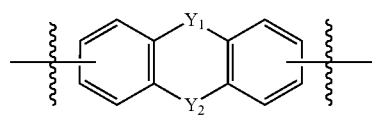

[Formula 3b]

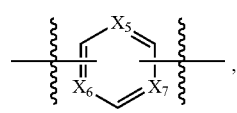, wherein each of $X_5$ to $X_7$ is independently N or $CR_1$,
wherein each of $Y_1$ and $Y_2$ is independently selected from a single bond, O, S, Se, $Si(R_2)(R_4)$, and $C(R_3)(R_5)$, and
wherein each of $R_1$, $R_2$, $R_3$, $R_4$ and $R_5$ is independently selected from the group consisting of hydrogen, deuterium, cyano group, hydroxyl group, halogen, a substituted or non-substituted C1 to C10 alkyl group, a substituted or non-substituted C6 to C20 aryl group and a substituted or non-substituted C3 to C30 heteroaryl group.

9. The electroluminescent device of claim 1, wherein R and R' are hydrogen.

10. An electroluminescent compound selected from Formula 5:

[Formula 5]

54

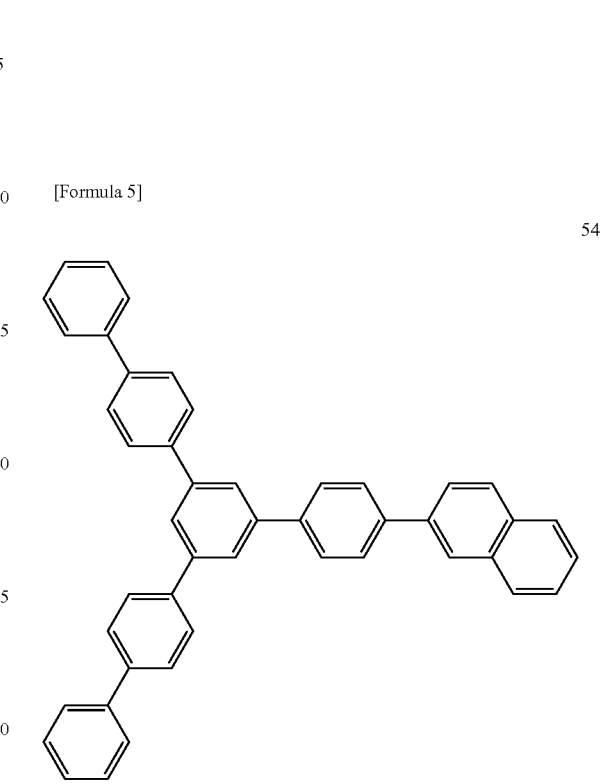

55

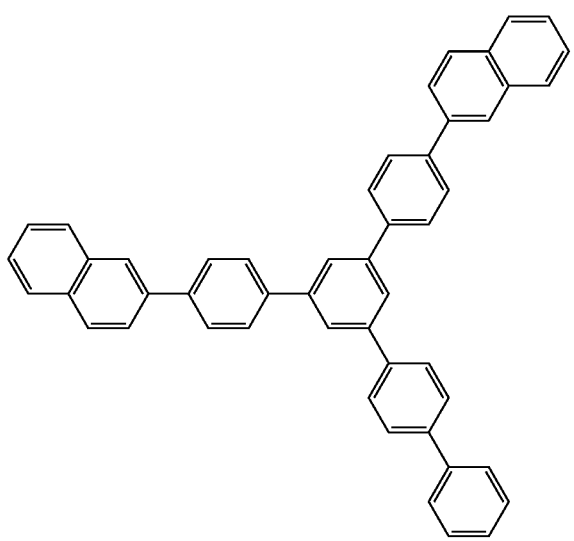

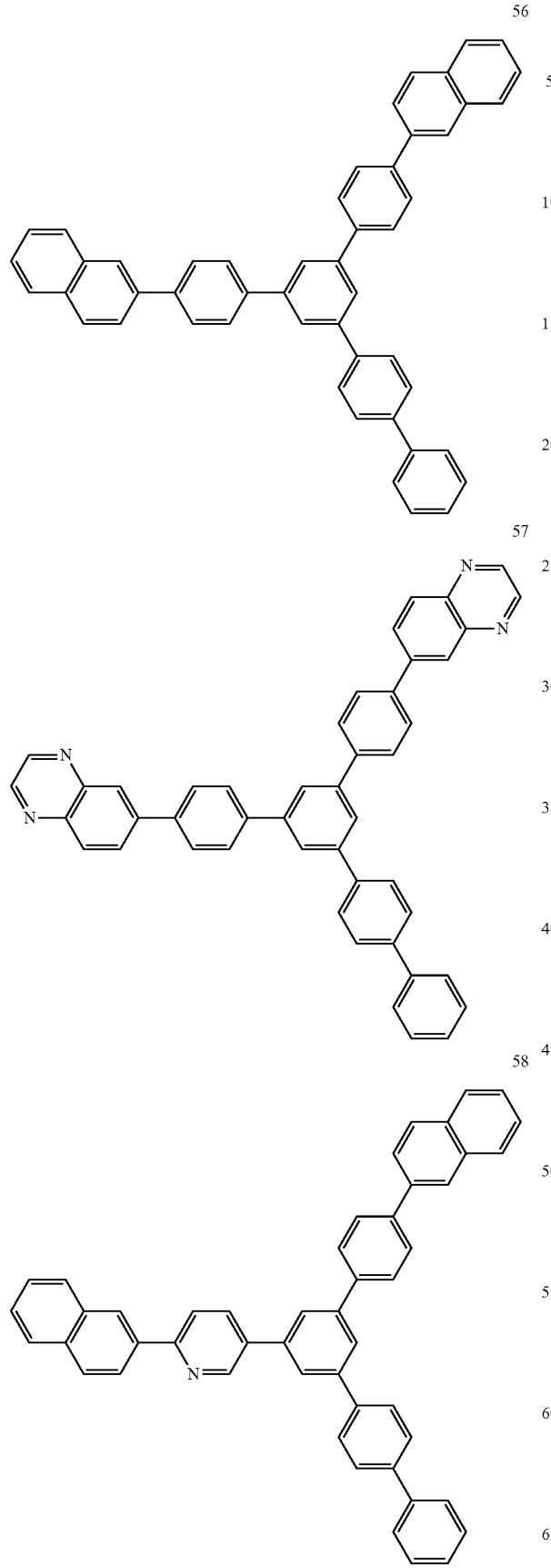
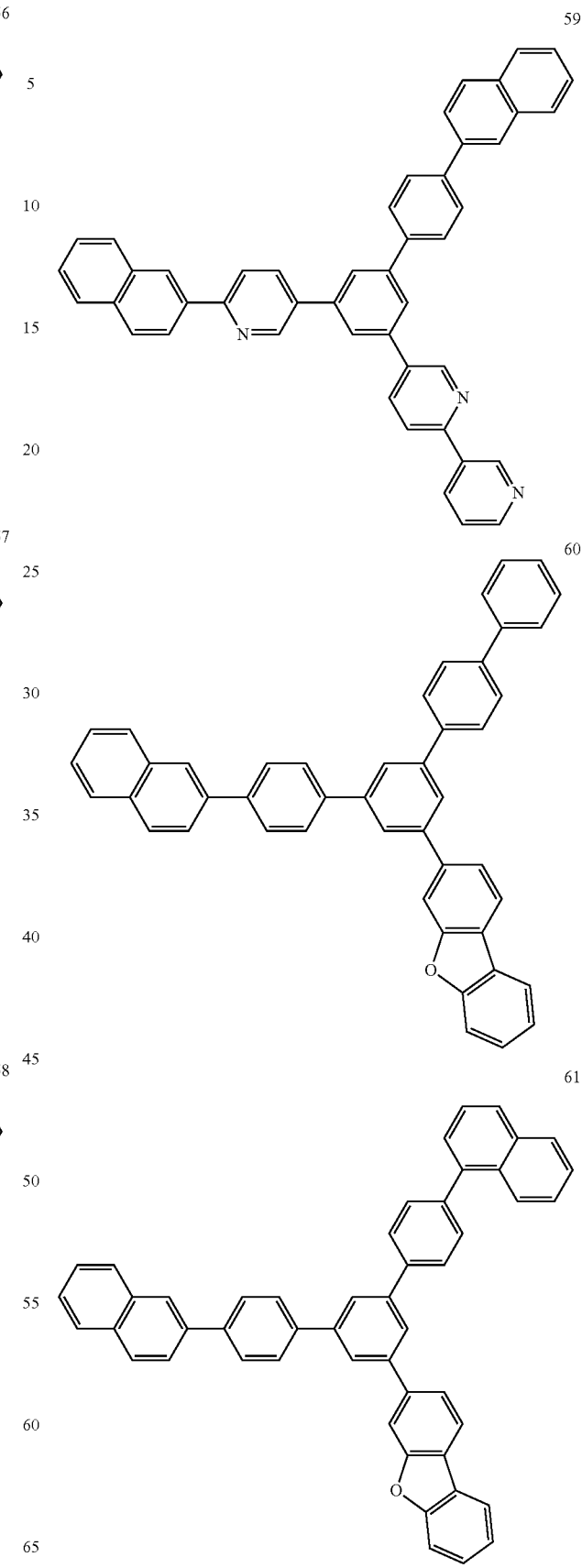

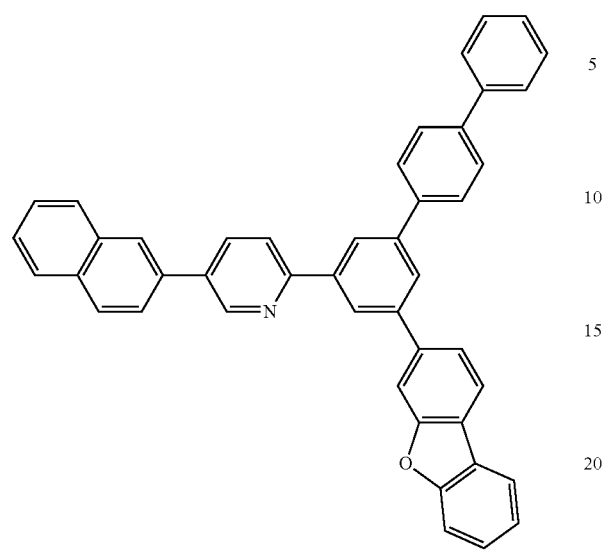
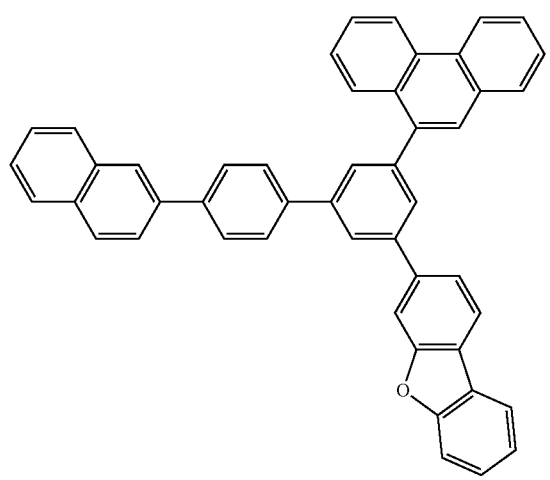
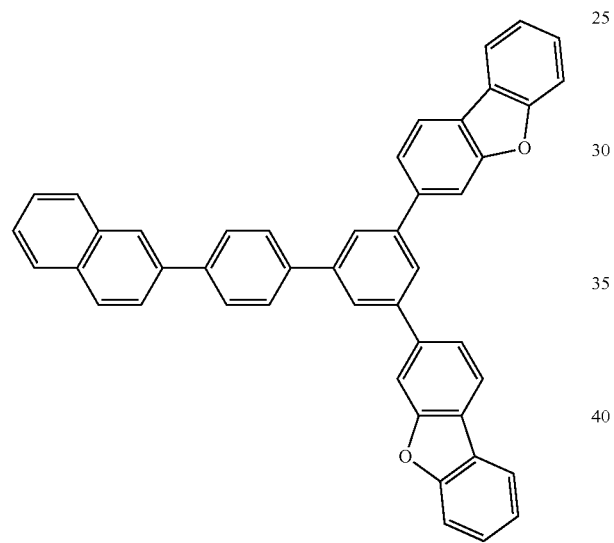
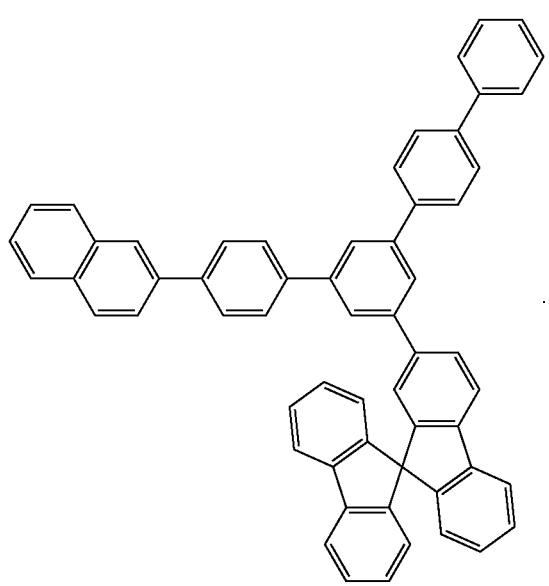
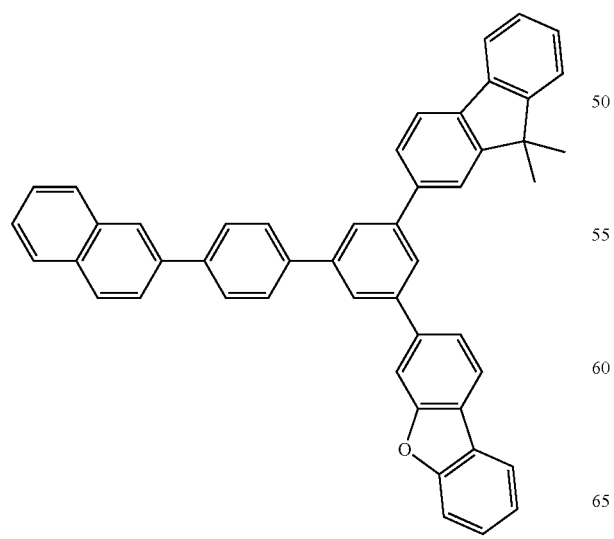

11. An electroluminescent compound selected from Formula 5:
[Formula 5]
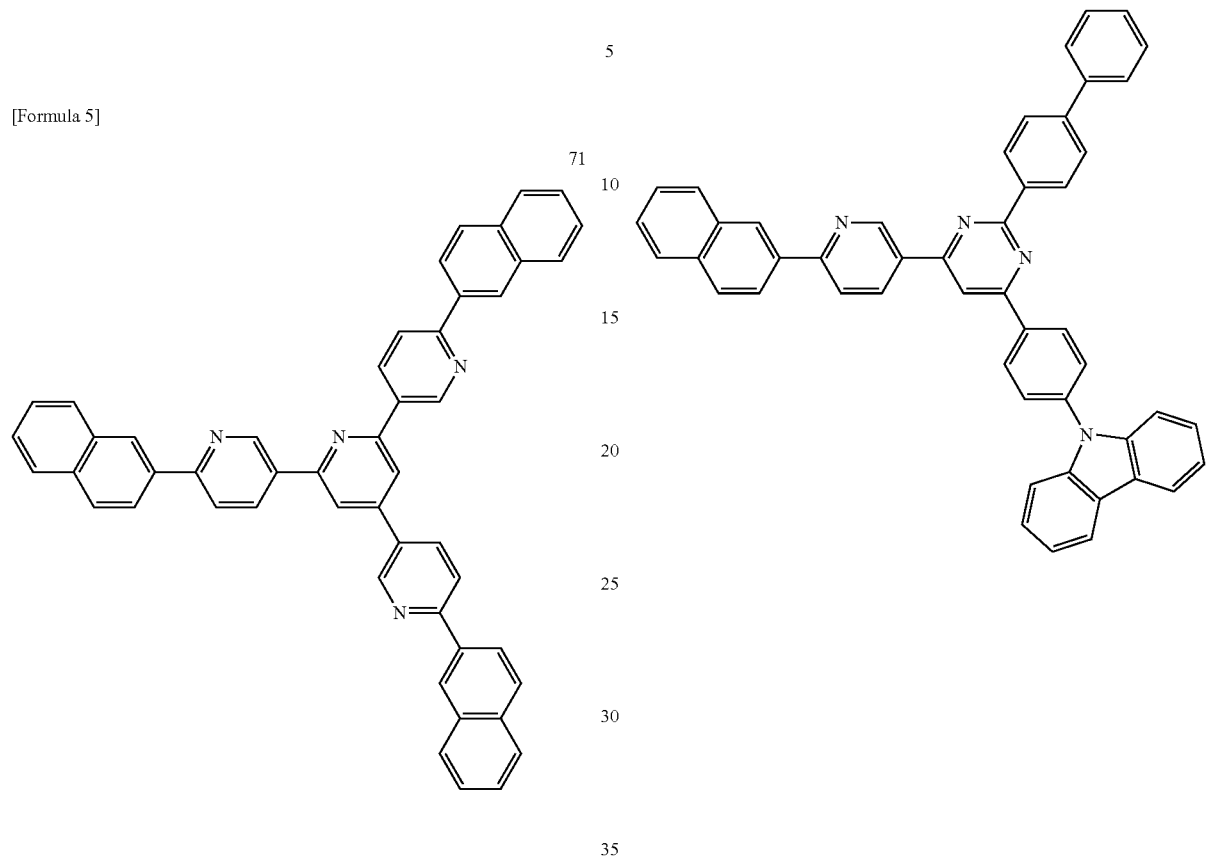
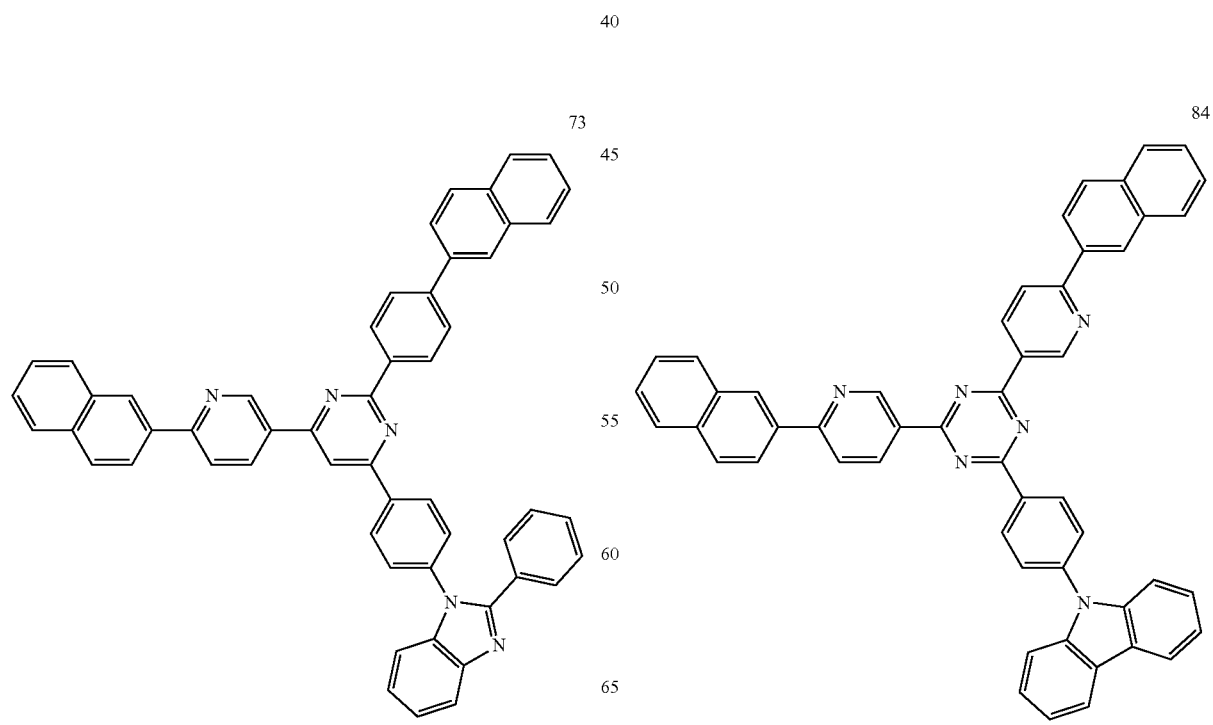

-continued

86
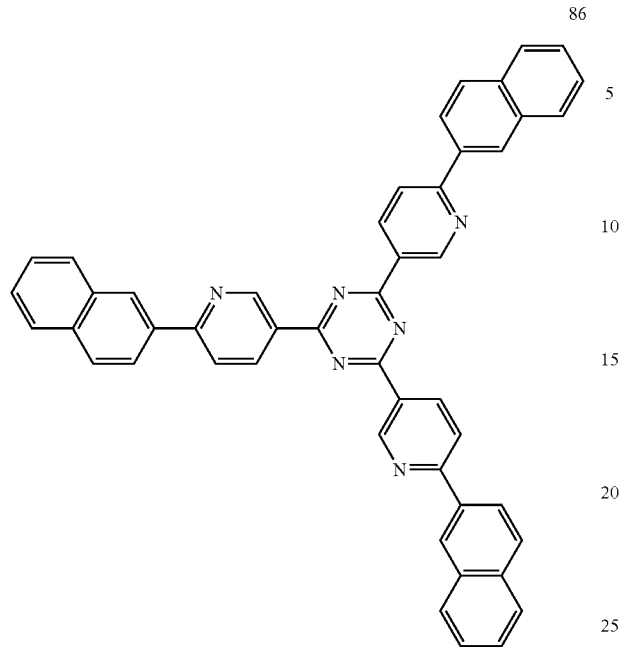

87
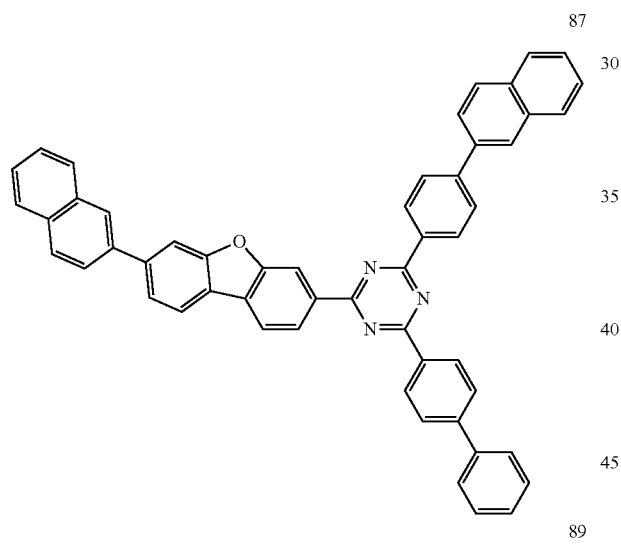

89
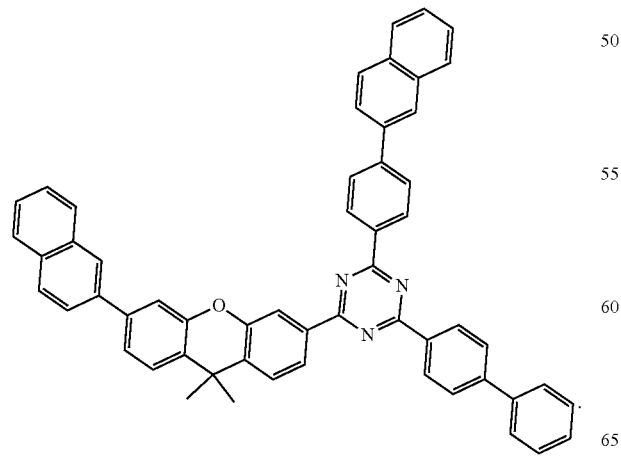

12. An electroluminescent device, comprising:
a first electrode;
a second electrode facing the first electrode;
at least one organic material layer between the first and second electrodes and including an electron injection layer, an electron transporting layer, a hole injection layer, a hole transporting layer, an electron blocking layer, a hole blocking layer and an emitting material layer, and
a light-efficiency enhancing layer on a side of one of the first electrode and the second electrode, the light-efficiency enhancing layer is positioned to be opposite to the organic material layer,
wherein one or more of the hole transporting layer and light-efficiency enhancing layer includes an electroluminescent compound of Formula 2:

[Formula 2]
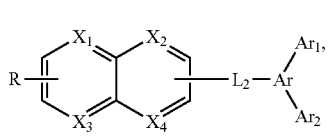

wherein each of $X_1$ to $X_4$ is independently N or CR',
wherein each of R and R' is independently selected from the group consisting of hydrogen, deuterium, cyano group, hydroxyl group, halogen, a substituted or non-substituted C1 to C10 alkyl group, a substituted or non-substituted C6 to C20 aryl group and a substituted or non-substituted C3 to C30 heteroaryl group,
wherein $L_2$ is selected from a single bond, a substituted or non-substituted C6 to C20 arylene group and a substituted or non-substituted C3 to C30 heteroarylene group,
wherein Ar is selected from the group consisting of a substituted or non-substituted C6 to C20 arylene group and a substituted or non-substituted C3 to C30 heteroarylene group, and
wherein each of $Ar_1$ and $Ar_2$ is independently selected from the group consisting of a substituted or non-substituted C6 to C20 aryl group and a substituted or non-substituted C3 to C30 heteroaryl group.

13. The electroluminescent device according to claim 12, wherein the electroluminescent compound is selected from Formula 5:

[Formula 5]
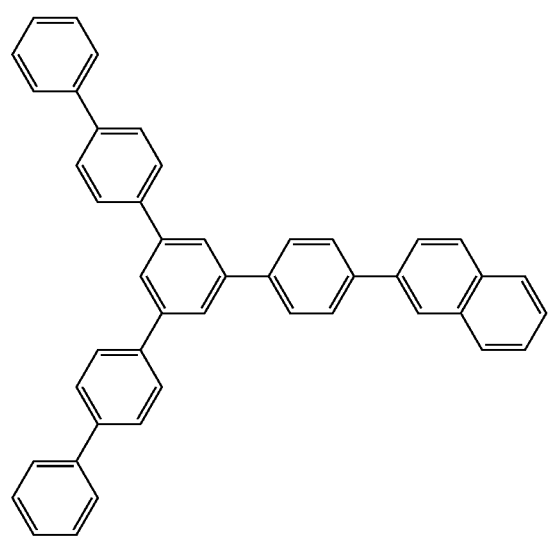
54
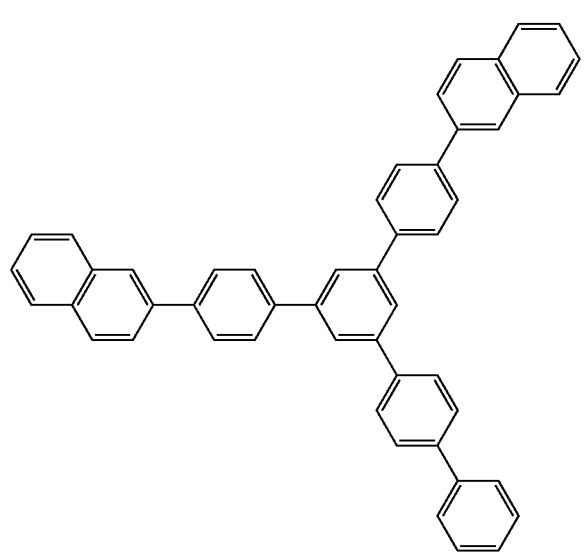
55
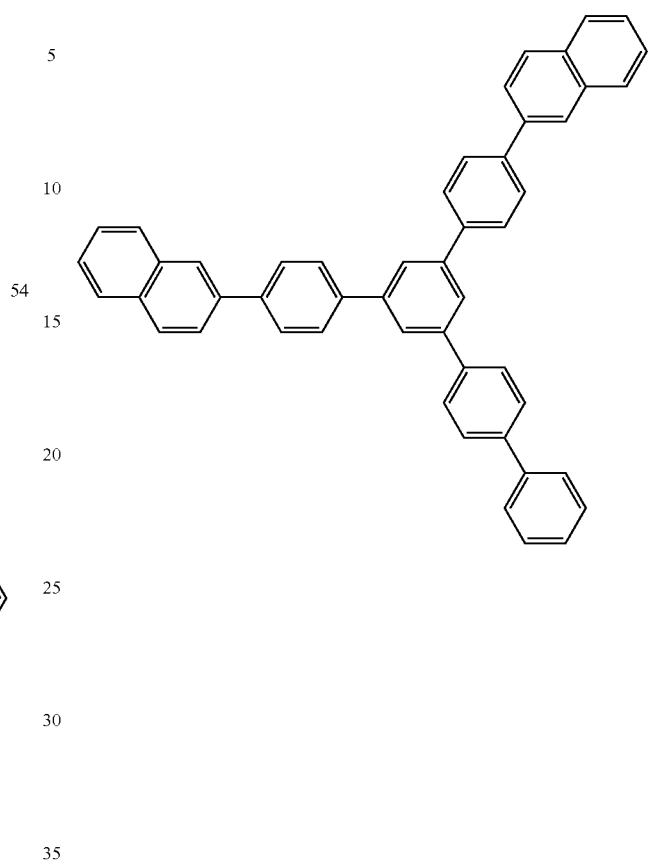
56
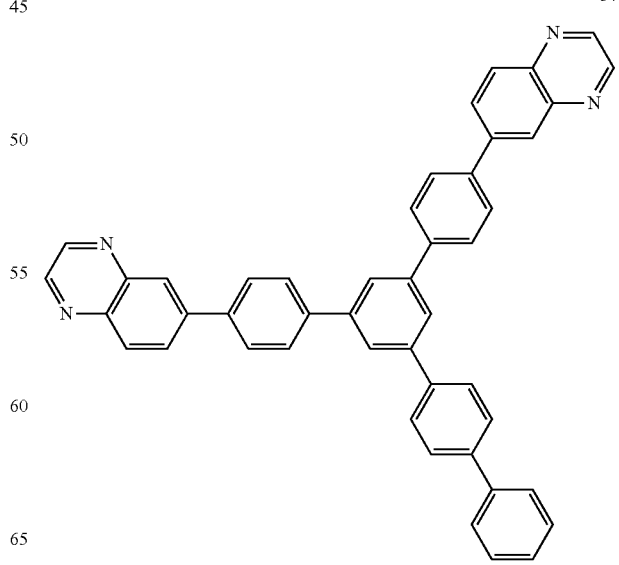
57

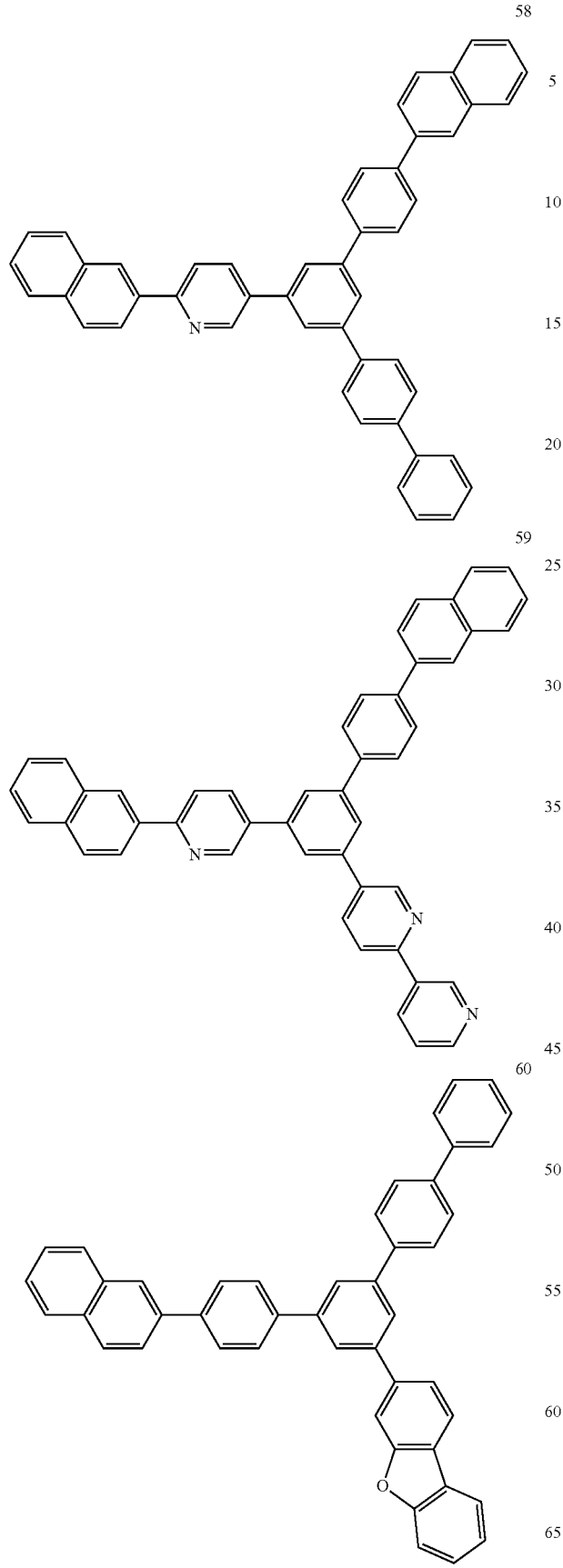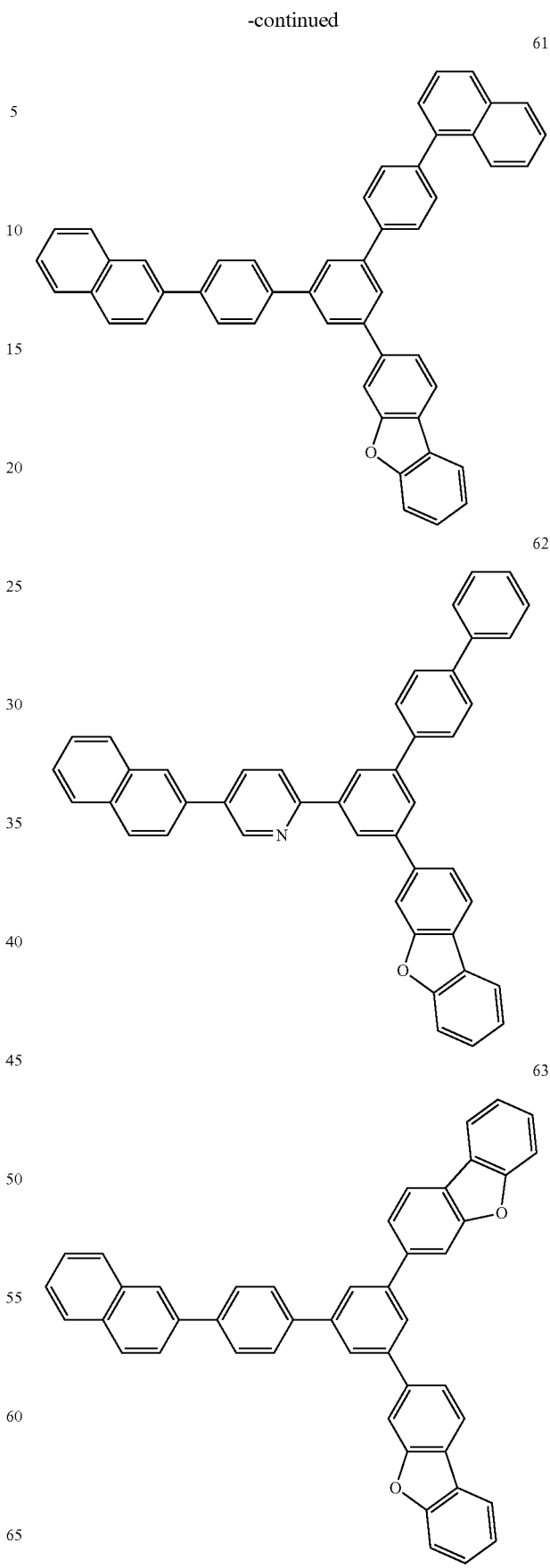

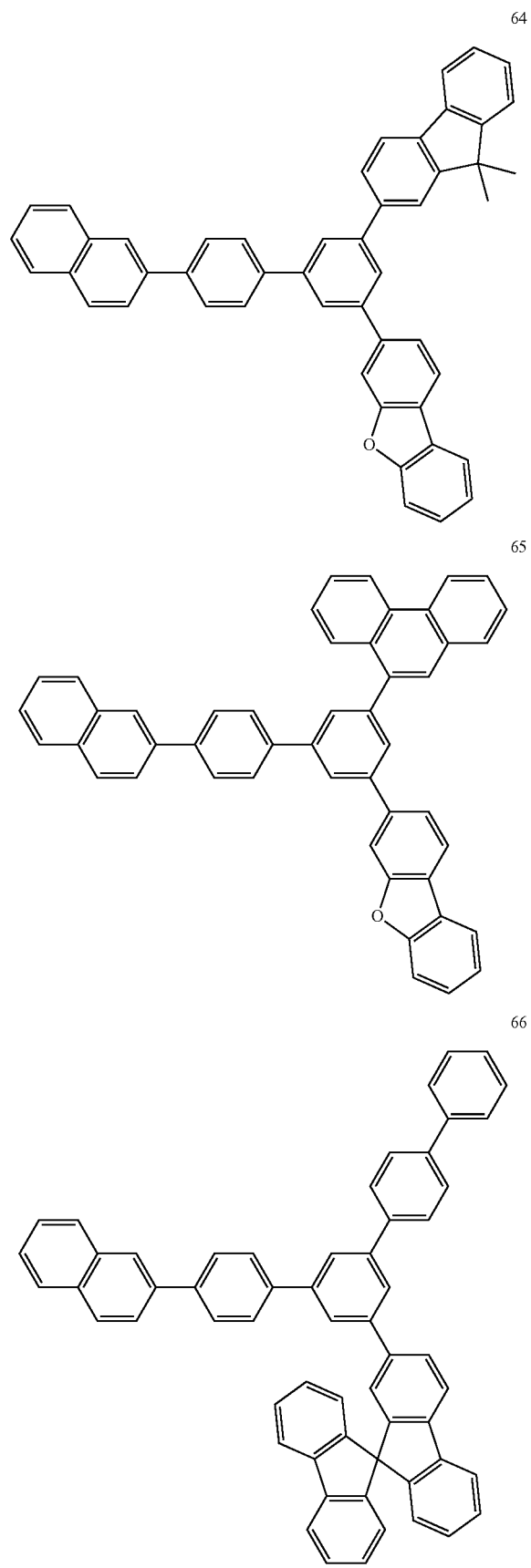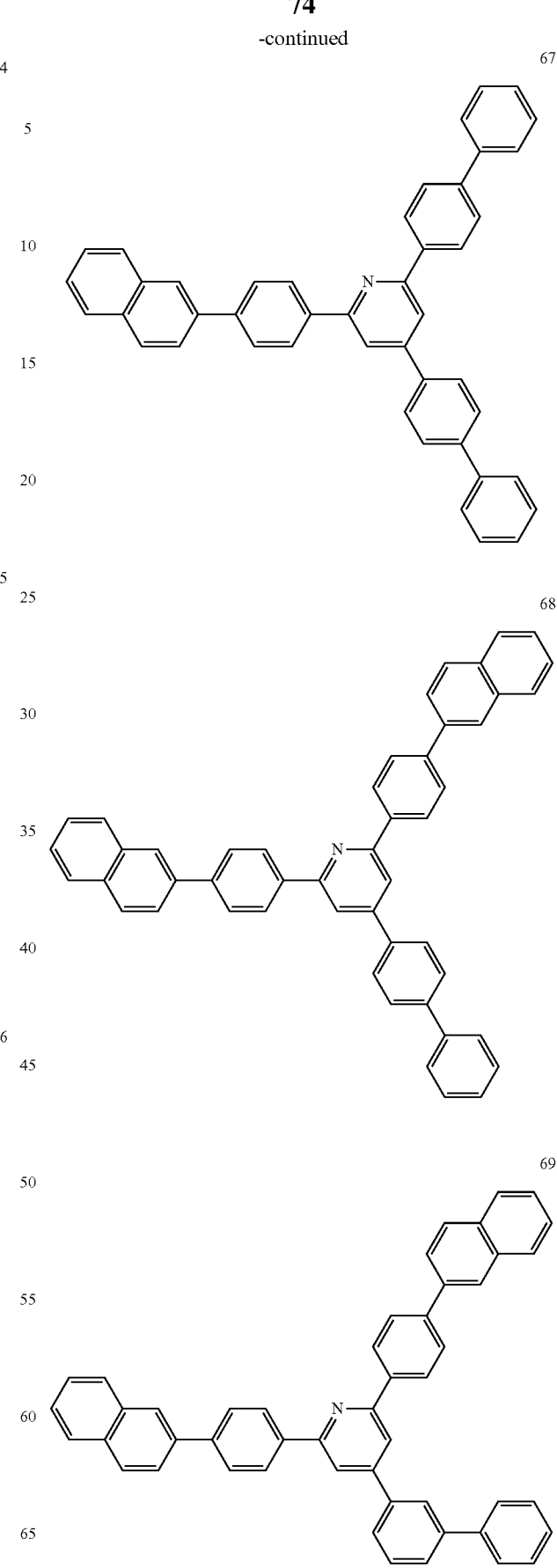

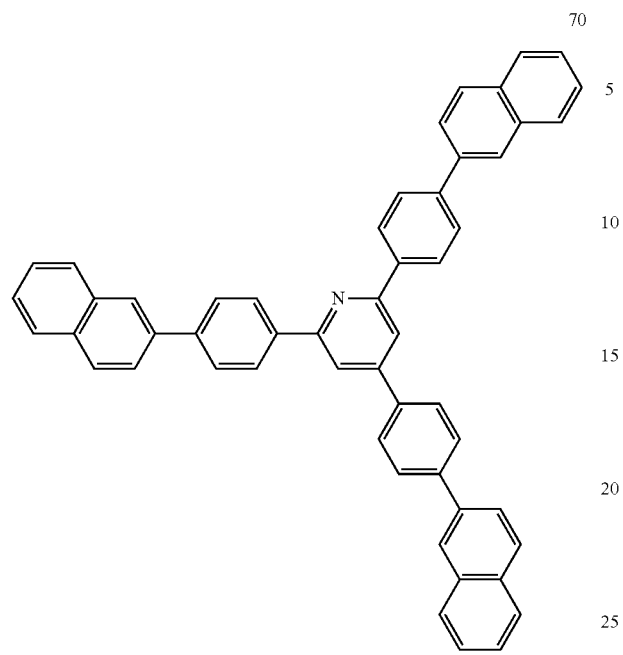
70
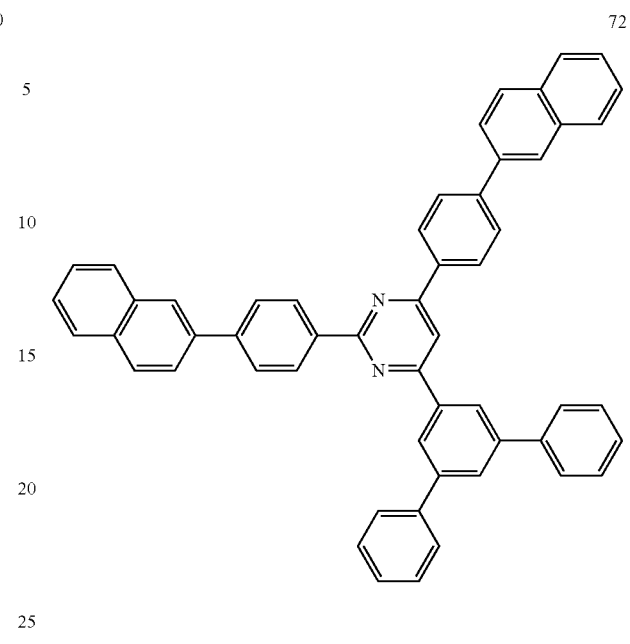
72
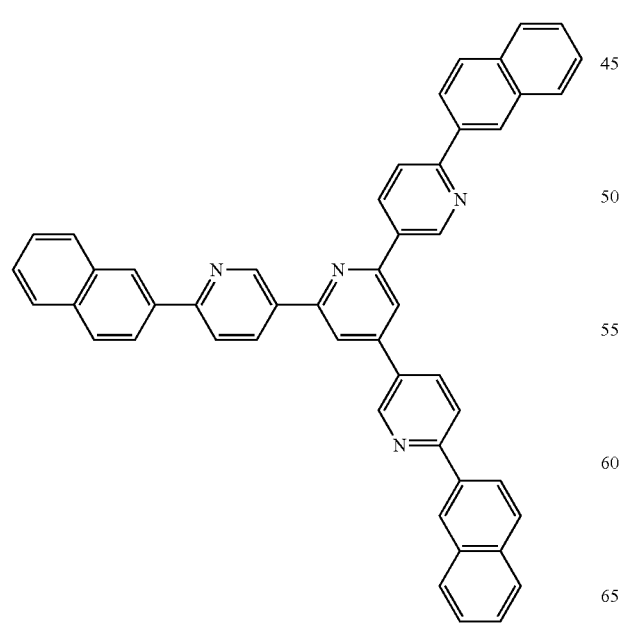
71
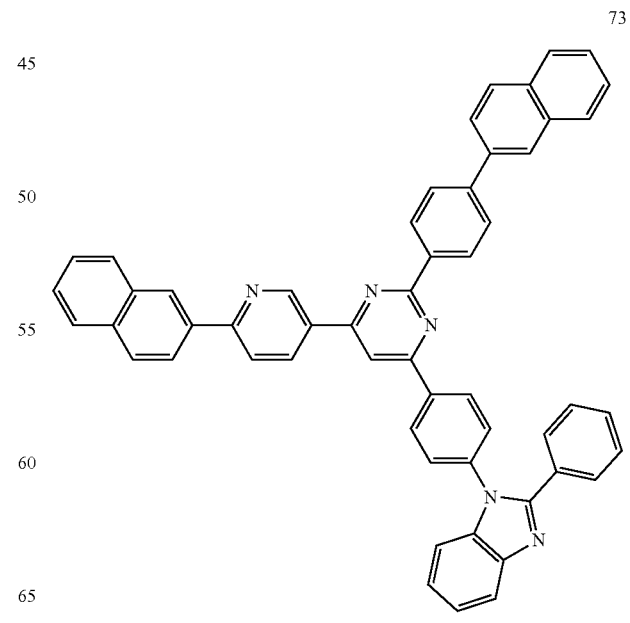
73

74
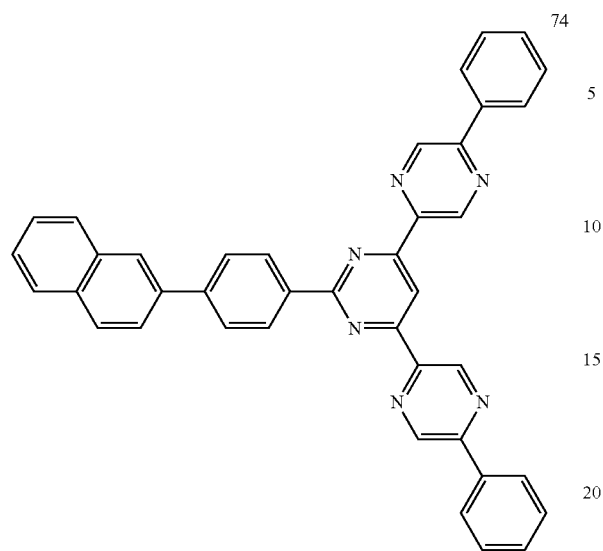
75
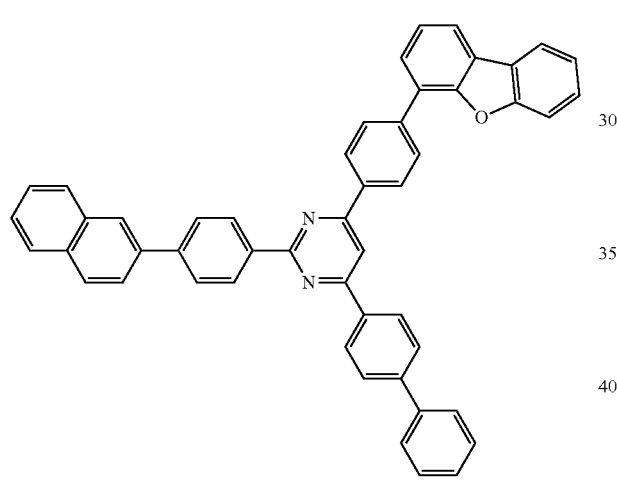
76
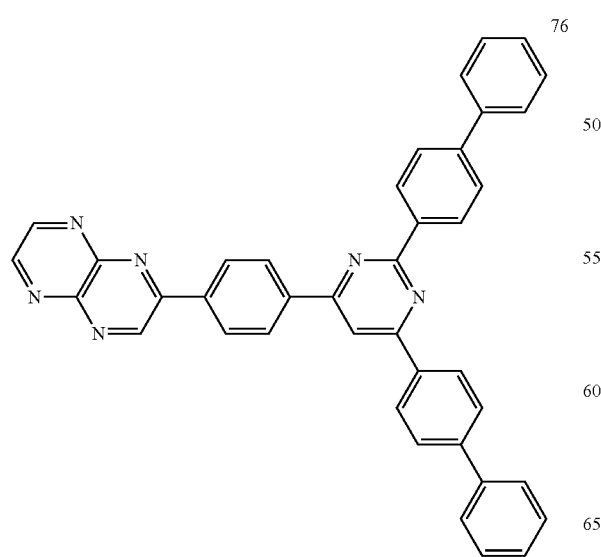
77
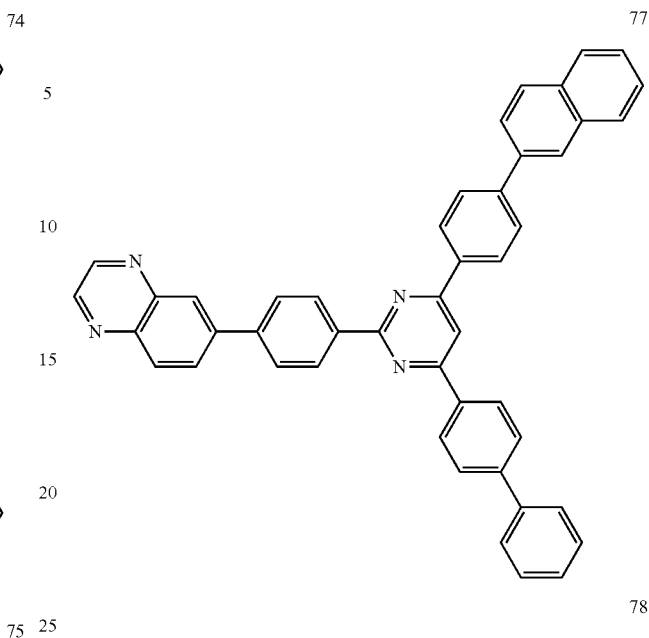
78
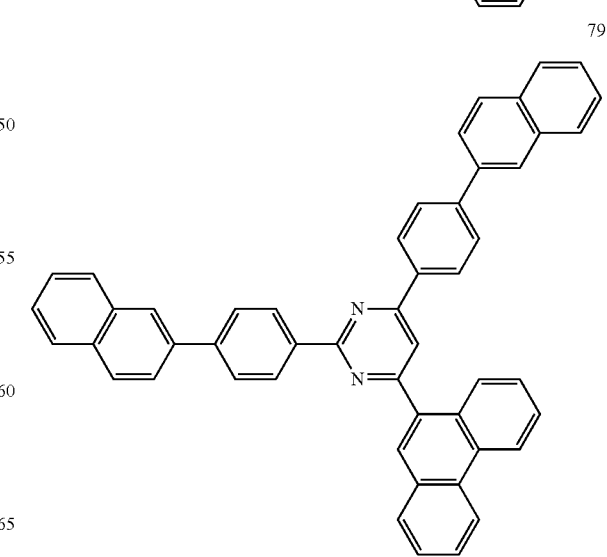
79

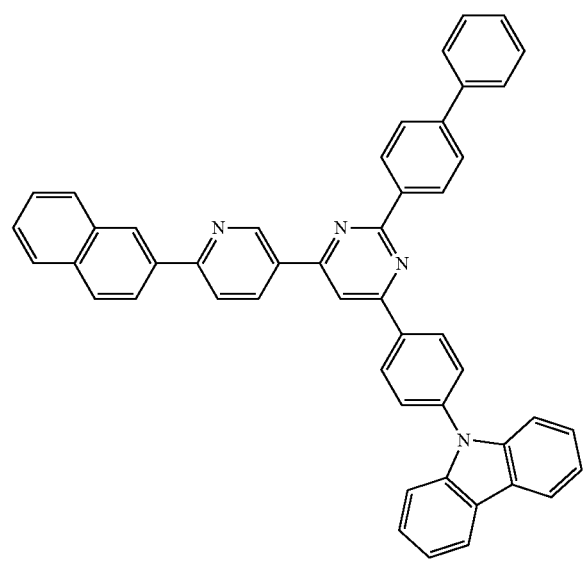
80
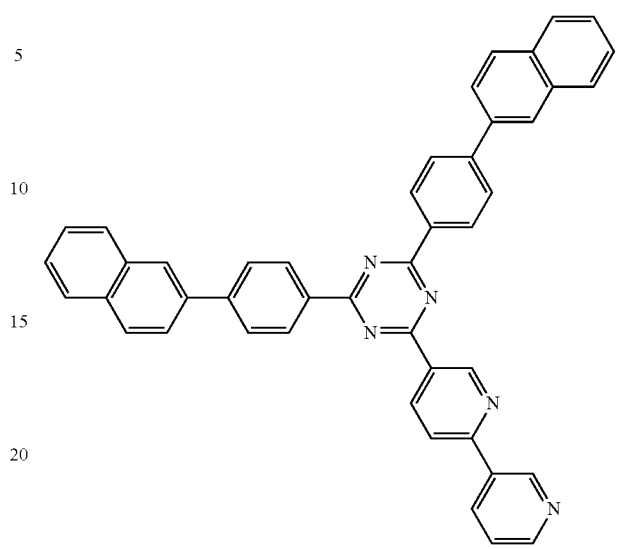
82
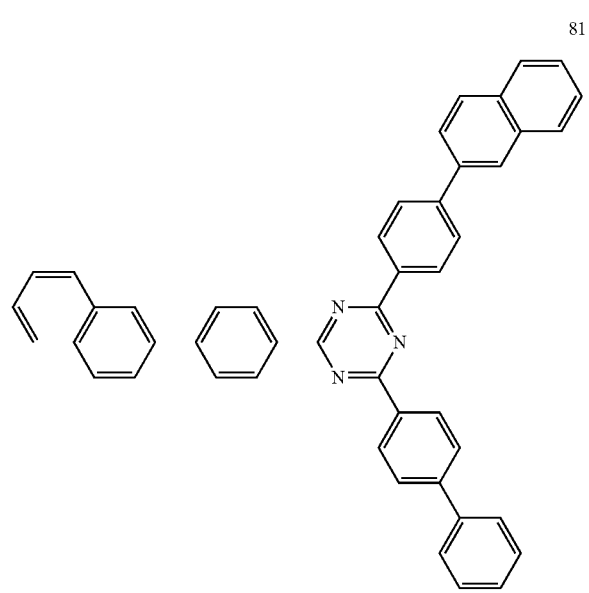
81
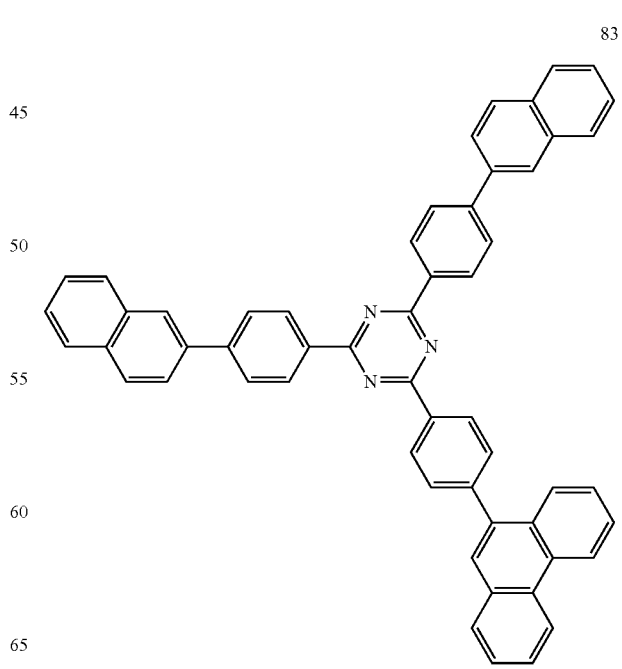
83

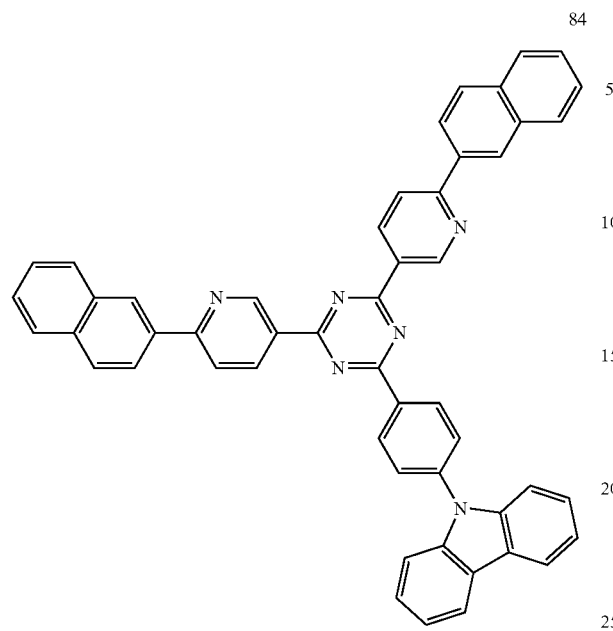
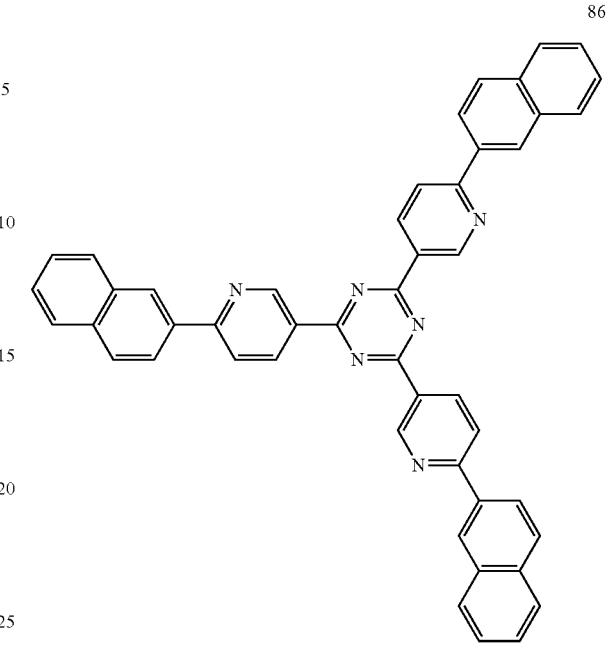
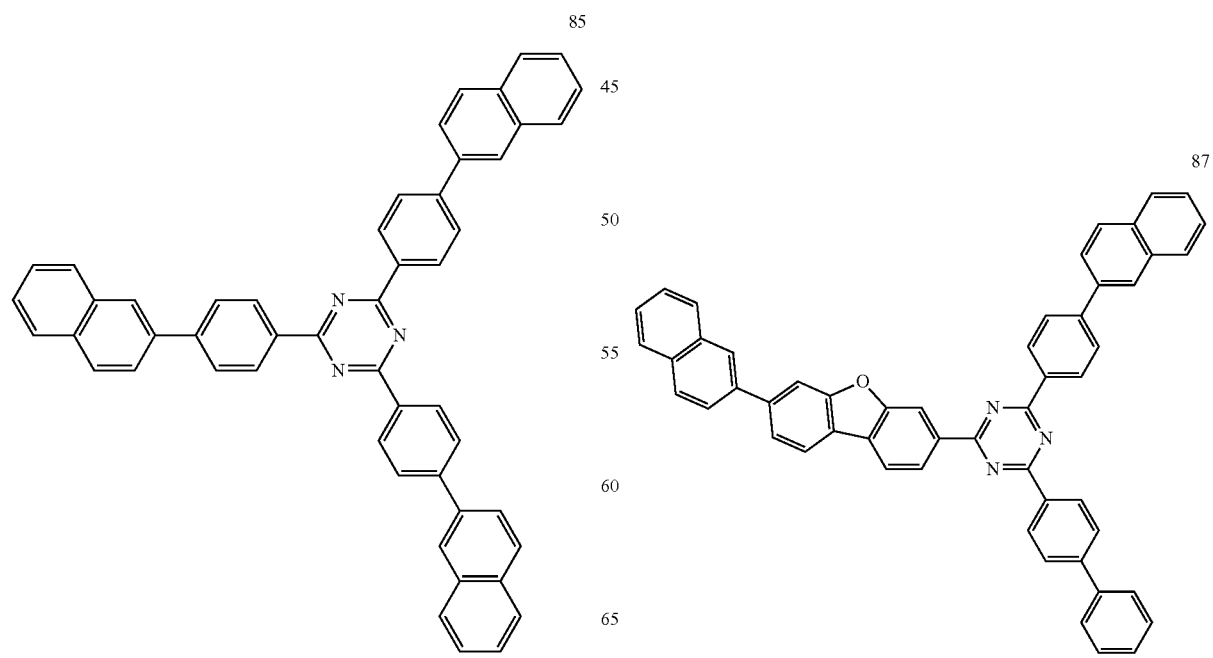

88
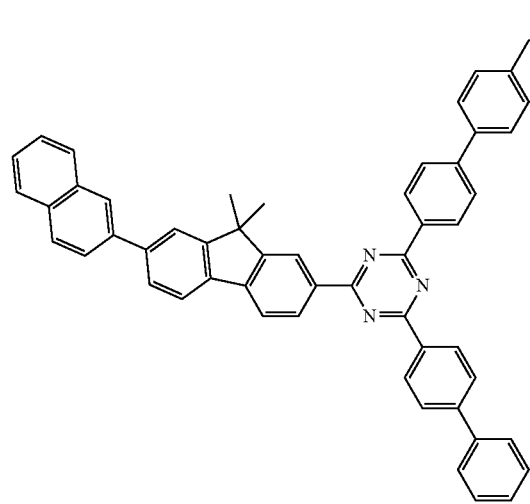
89
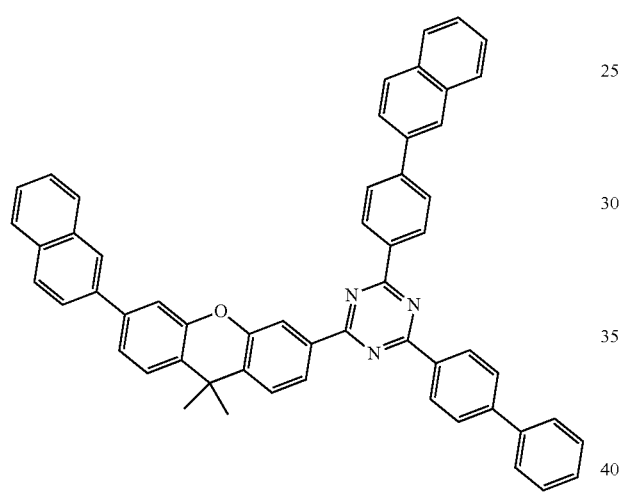
90
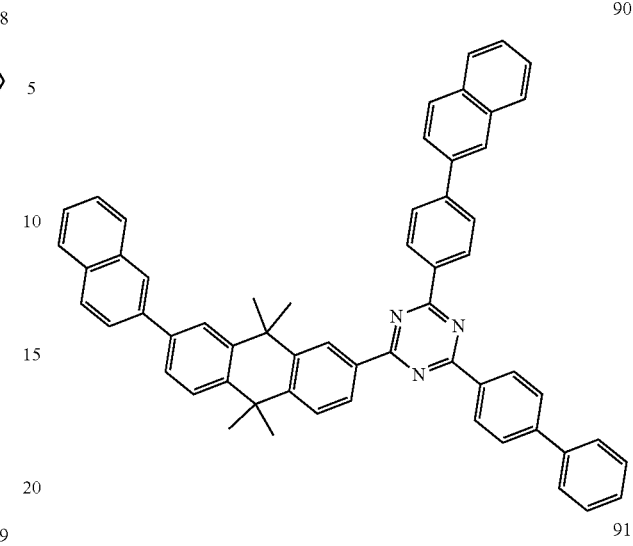
91
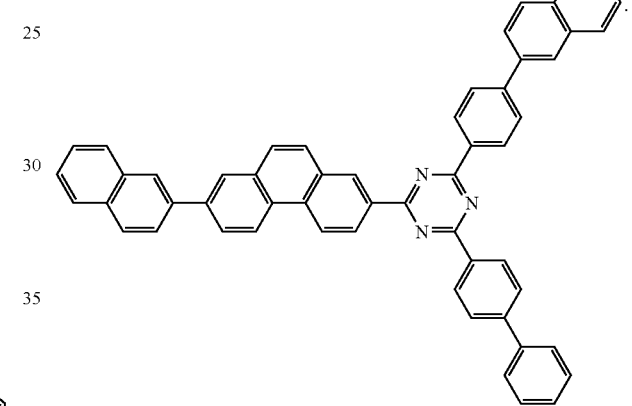
* * * * *